United States Patent
Tooma et al.

(10) Patent No.: US 6,957,583 B2
(45) Date of Patent: Oct. 25, 2005

(54) ULTRASONIC ARRAY SENSOR, ULTRASONIC INSPECTION INSTRUMENT AND ULTRASONIC INSPECTION METHOD

(75) Inventors: Masahiro Tooma, Kanasago (JP); Naoyuki Kono, Mito (JP); Masahiro Koike, Hitachi (JP); Hirokazu Adachi, San Francisco, CA (US); Takao Shimura, Hitachi (JP); Makoto Senoo, Tokai (JP); Tetsuya Matsui, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 15 days.

(21) Appl. No.: 10/696,564

(22) Filed: Oct. 30, 2003

(65) Prior Publication Data

US 2004/0118210 A1 Jun. 24, 2004

(30) Foreign Application Priority Data

Oct. 31, 2002 (JP) ........................ 2002-316971

(51) Int. Cl.[7] ................... G01N 29/04; A61B 8/02
(52) U.S. Cl. .................. 73/625; 73/628; 73/641; 600/448
(58) Field of Search .................. 73/625, 597, 598, 73/600, 602, 626, 628, 641; 600/447, 448

(56) References Cited

U.S. PATENT DOCUMENTS

| 4,258,574 | A | * | 3/1981 | Hildebrand et al. | .......... 73/625 |
| 4,531,411 | A | * | 7/1985 | Collins et al. | ................ 73/603 |
| 5,014,712 | A | * | 5/1991 | O'Donnell | ................... 600/447 |
| 6,055,861 | A | * | 5/2000 | Banta et al. | ................... 73/626 |
| 6,146,328 | A | * | 11/2000 | Chiao et al. | ................ 600/443 |
| 6,202,489 | B1 | * | 3/2001 | Beffy et al. | .................... 73/628 |
| 6,645,146 | B1 | * | 11/2003 | Adams et al. | .............. 600/443 |

FOREIGN PATENT DOCUMENTS

| JP | P2001-228126 | 8/2001 |
| JP | P2001-228128 | 8/2001 |
| JP | P2002-62281 | 2/2002 |

* cited by examiner

Primary Examiner—Hezron Williams
Assistant Examiner—Jacques M. Saint-Surin
(74) Attorney, Agent, or Firm—McDermott Will & Emery LLP

(57) ABSTRACT

An ultrasonic inspection instrument for detecting a crack and performing sizing in the depth direction of the crack. By a transmitter element array and a receiver element array included in a common sensor, focus points between focused acoustic fields are electronically scanned in a range including a location where half the sum of the transmitting angle of ultrasonic waves to an inspection-target material and the receiving angle of diffraction echoes from the inspection-target material is 30 degrees, so that a tip portion of the crack is detected from the received diffraction echoes. Thus, the detectability of the ultrasonic inspection instrument for detecting diffraction waves in a subject to be inspected and performing crack inspection is stabilized and kept high.

20 Claims, 18 Drawing Sheets

ULTRASONIC ARRAY SENSOR, ULTRASONIC INSPECTION INSTRUMENT AND ULTRASONIC INSPECTION METHOD

BACKGROUND OF THE INVENTION

The present invention relates to the field of ultrasonic inspection technology.

As known in the related art (e.g. see JP-A-2001-228128), there is an instrument in which two ultrasonic probes, that is, a transmitter probe and a receiver probe are fixedly disposed at a fixed distance and a crack inside a subject to be inspected is ultrasonically inspected using a TOFD (Time of Flight Diffraction) technique; the TOFD technique is defined in British Standard BS7706 (1993); and according to the TOFD technique, the incident angle with which an ultrasonic wave transmitted from the transmitter probe enters the subject to be inspected is set to be in a range of from 45 degrees to 55 degrees while the receiving angle with which a diffraction echo derived from the ultrasonic wave and coming from a tip of a crack in the subject to be inspected is also set to be in a range of from 45 degrees to 55 degrees.

However, there is a fear that the intensity of the diffraction echo is lowered due to the divergence of the transmitted ultrasonic beam so that the performance of crack detection deteriorates. As a technique for wiping out such a fear, known are JP-A-2001-228128 (see pages 2–4 and FIGS. 1–8) and JP-A-2001-228126 (see pages 4–5 and FIGS. 1–4) in which an ultrasonic beam transmitted from a transmitter probe is converged to irradiate the tip of a crack therewith, and the diffraction echo detection area of a receiver probe is also converged to detect the diffraction echo efficiently.

In order to detect the diffraction echo efficiently, it is known that it is preferable in view of efficiency that the incident angle of the ultrasonic wave is 45 degrees, as disclosed in JP-A-2001-228126 (see pages 4–5 and FIG. 2).

Further, JP-A-2002-62281 (see pages 3–6 and FIGS. 1–12) discloses a technique in which an element set having a plurality of elements assembled in the form of a transmitter element array and a receiver element array to be mounted in one and the same casing is used while a delay circuit is connected to each element of the element set so as to gradually shift the timing for the delay circuit to excite the element. Thus, the angle of refraction of ultrasonic waves is finely adjusted through electronic scan while the traveling direction of the ultrasonic waves is controlled. In such a manner, the depth of a crack is measured.

In these conventional examples, ultrasonic inspection is carried out in the TOFD (Time of Flight Diffraction) technique in which two ultrasonic probes, that is, a transmitter probe and a receiver probe are fixed at a fixed distance, and further both the incident angle and the receiving angle of ultrasonic waves are set to be in a range of from 45 degrees to 55 degrees. The reason why those angles are regulated to be 45–55 degrees is as follows. That is, it has been heretofore considered that a diffraction echo obtained by irradiation of a tip of a crack with an ultrasonic beam is intensive in the direction of 45–55 degrees. Thus, such a range has been generally adopted.

However, in the TOFD technique in which both the incident angle and the receiving angle of ultrasonic waves are set to be about 45–55 degrees, the ultrasonic transmitter probe and the ultrasonic receiver probe are fixedly disposed at a fixed distance wide enough to retain the transmitting and receiving angles in the range of from about 45 degrees to about 55 degrees. This results in increase of the total external dimensions of the ultrasonic transmitter probe and the ultrasonic receiver probe. Thus, there is a problem that this technique cannot be applied to ultrasonic inspection of a place to be inspected or a narrow portion small in foot print of each transmitter/receiver probe. In addition, there is a problem that the course of the ultrasonic waves from the transmitter side to the receiver side is so long that the intensity of the received ultrasonic waves becomes weak.

SUMMARY OF THE INVENTION

It is therefore an object of the invention to detect any crack surely over a range from a shallow position to a deep position in a subject to be inspected, and more preferably to attain ultrasonic inspection surely even on a subject to be inspected with large attenuation of ultrasonic waves.

In order to attain the foregoing object, the present invention proposes a configuration of an array sensor of an ultrasonic inspection instrument including both a transmitter element array in which a plurality of transmitter elements for transmitting ultrasonic waves are arrayed and a receiver element array in which a plurality of receiver elements for receiving ultrasonic waves are arrayed, wherein the elements of the element arrays are arrayed so that each of the elements is 0.1 mm to 2 mm wide and adjacent ones of the elements in each of the element arrays are at a distance of 0.05 mm to 0.2 mm from each other. In addition to such a configuration, preferably, the present invention proposes that friction reduction means abutting against the subject to be inspected is placed in the array sensor clear of the entrance/exit surface of ultrasonic waves.

In addition, the present invention proposes a configuration of an ultrasonic inspection instrument including a control unit for focusing ultrasonic waves transmitted from the transmitter elements on a focus point where half the sum of a transmitting angle and a receiving angle will be not larger than 30 degrees, generation means for generating inspection information based on the ultrasonic waves received by the receiver elements; and display means for displaying the inspection information generated by the generation means.

Further, the present invention proposes an ultrasonic inspection method for controlling an ultrasonic inspection instrument, including the steps of: transmitting and receiving ultrasonic waves to and from a subject to be inspected, by means of an array sensor having both a transmitter element array in which a plurality of transmitter elements for transmitting ultrasonic waves are arrayed and a receiver element array in which a plurality of receiver elements for receiving ultrasonic waves are arrayed; and focusing the ultrasonic waves on a focus point where half the sum of a transmitting angle and a receiving angle involved in the transmission and reception is not larger than 30 degrees.

Other objects, features and advantages of the invention will become apparent from the following description of the embodiments of the invention taken in conjunction with the accompanying drawings.

BRIEF DESCRIPTION OF THE DRAWINGS

FIGS. 6-1 and 6-2 are explanatory views of definitions of a transmitting angle θt and a receiving angle θr;

DETAILED DESCRIPTION OF THE INVENTION

The present inventors manufactured an array sensor (hereinafter also referred to as "sensor" simply) in which an array-type transmitter ultrasonic transducer (hereinafter also referred to as "transmitter array sensor") having a transmitter element array in which a plurality of ultrasonic elements were arrayed and an array-type receiver ultrasonic transducer (hereinafter also referred to as "receiver array sensor") having a receiver element array in which a plurality of ultrasonic elements were arrayed were put into one casing and molded integrally. The present inventors used this sensor to irradiate a crack in a subject to be inspected with ultrasonic waves. In that event, focusing was applied to both transmission and reception of the ultrasonic waves and the transmitting and receiving angles of the ultrasonic waves were set to be in a range of from 0 degree to 30 degrees, which range had been heretofore regarded as a difficult range for a diffraction echo to be detected. Thus, the present inventors performed crack inspection and crack sizing tests.

As a result, the present inventors made it clear for the first time that crack inspection and crack sizing could be carried out well. That is, the present inventors had discovered that crack inspection and crack sizing could be carried out satisfactorily even when the transmitting/receiving angle of ultrasonic waves was shallow to be not larger than 30 degrees while the angle had been heretofore in a range of from 45 degrees to 55 degrees.

That is, there could be established a novel ultrasonic inspection method different from any conventional TOFD technique in which the transmitting/receiving angle of ultrasonic waves was in a range of from 45 degrees to 55 degrees. This novel ultrasonic inspection method could attain so-called robustness in crack detectability. The robustness is characterized in that crack detection and crack sizing can be carried out stably and achieved in such a manner that the range where the incident angle of transmission/reception is not larger than 30 degrees is used so that the crossing range between a transmitter focus point and a receiver focus point can be expanded and the fluctuation of crack detectability due to slight misalignment between the transmitter ultrasonic focus point and the receiver ultrasonic focus point can be reduced on a large scale.

Use of this novel ultrasonic inspection method opens the way for the following crack detection and crack sizing, that cannot be carried out in tip echo techniques or TOFD techniques conventionally, such as (1) a crack narrow in width and weak in ultrasonic diffraction intensity, (2) a crack in a material where ultrasonic waves are attenuated greatly or an anisotropic material where ultrasonic waves are redirected, (3) a crack in a place to be inspection or a narrow portion small in foot print of a probe, and (4) a crack in weld melt.

Figure 1:
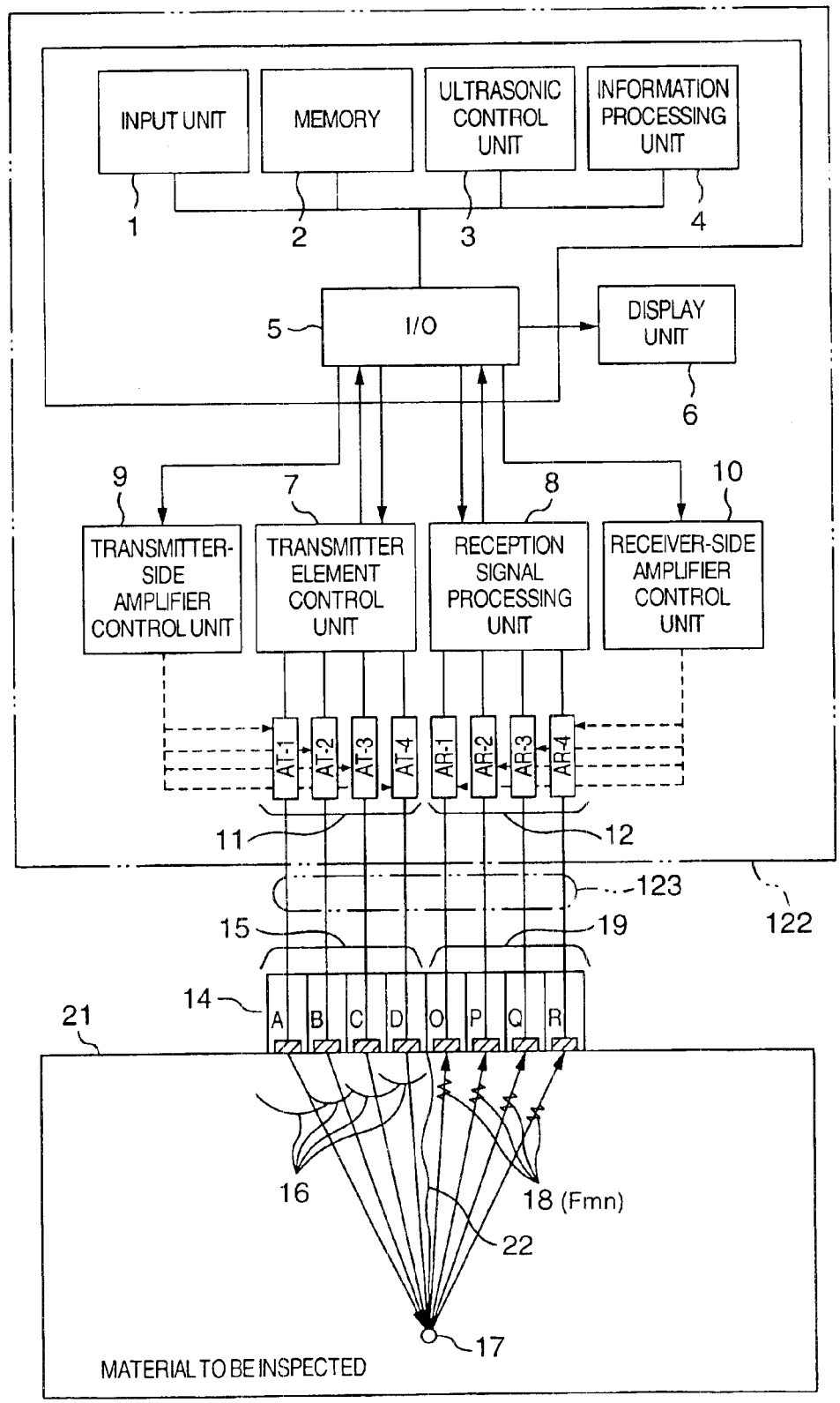
FIG. 1 is a diagram of the total configuration of an ultrasonic inspection instrument according to an embodiment of the present invention.

A specific embodiment for implementing this novel ultrasonic inspection method will be described below. FIG. 1 shows the total configuration of an ultrasonic inspection instrument according to the present invention. The ultrasonic inspection instrument according to the embodiment of the present invention is generally constituted by an ultrasonic inspection instrument body 122 and an array sensor 14 (hereinafter referred to as "sensor 14" simply) electrically connected to the ultrasonic inspection instrument body 122 through signal lines. The signal lines are bundled and formed into a signal cable 123.

In the sensor 14, elements A, B, C and D of a transmitter element array 15 constituting a transmitter array sensor transmit ultrasonic waves 16 into an inspection-target material 21 which is a subject to be inspected, respectively. The ultrasonic waves 16 are diffracted on the lower tip of a crack 22 in the inspection-target material 21. Elements O, P, Q and R of a receiver element array 19 constituting a receiver array sensor receive diffraction echoes 18 generated thus from the ultrasonic waves 16. Electric signals generated in the respective elements in accordance with the diffraction echoes 18 received from the elements of the receiver element array 19 are supplied to the ultrasonic inspection instrument body 122. The elements A, B, C and D of the transmitter element array 15 can be defined as transmitter elements because they are used for transmission. On the other hand, the elements O, P, Q and R of the receiver element array 19 can be defined as receiver elements because they are used for reception.

The sensor 14 having the transmitter element array 15 and the receiver element array 19 integrally is placed on the surface of the inspection-target material 21 so that the central portion of the sensor 14 is located just above the crack 22.

The ultrasonic inspection instrument body 122 creates an inspection result as an ultrasonic inspection result in response to the electric signals received from the elements of the receiver element array 19. The ultrasonic inspection instrument body 122 includes an input unit 1, a memory 2, an ultrasonic control unit 3, an information processing unit 4, an I/O 5, a display unit 6, a transmitter-side amplifier control unit 9, a receiver-side amplifier control unit 10, a transmitter element control unit 7, a reception signal processing unit 8, transmitter-side amplifiers 11 and receiver-side amplifiers 12.

Figure 2:
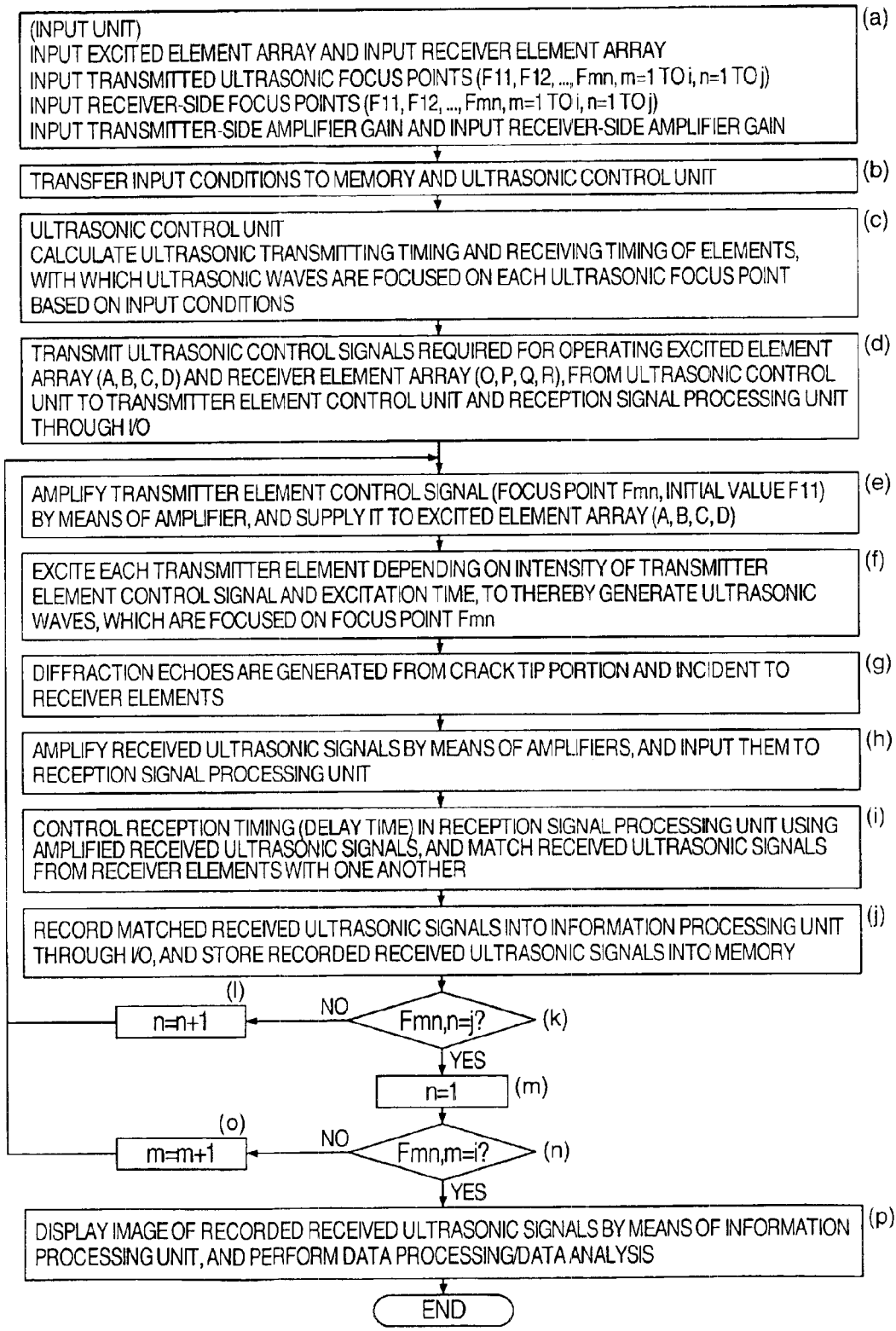
FIG. 2 is a flow chart of the operation of the ultrasonic inspection instrument according to the embodiment of the present invention.

The respective units and their roles will be described below in detail. FIG. 1 shows a diagram of the total configuration of the ultrasonic inspection instrument according to the embodiment of the present invention. FIG. 2 shows the flow of operating steps in the embodiment of the present invention.

First, input conditions for determining a transmitting/receiving pattern of ultrasonic waves are input by means of the input unit 1 (Step a). The input conditions are conditions for determining an ultrasonic transmitting/receiving pattern in order to detect a crack with high sensitivity. The input conditions include (1) the elements A, B, C and D which are set as elements in a transmitter element array (mentioned as an excited element array in FIG. 2), (2) the elements O, P, Q and R which are set as elements in a receiver element array, (3) the position of a transmitter ultrasonic focus point (F11, F12, ..., Fmn, m=1 to i, and n=1 to j), (4) the position of a receiver-side focus point (F11, F12, ..., Fmn, m=1 to i, and n=1 to j), (5) the gain indicating the amplification of each transmitter-side amplifiers 11, (6) the gain indicating the amplification of each receiver-side amplifiers 12, and so on. The input conditions are transferred from the input unit 1 to the memory 2 and the ultrasonic control unit 3 (Step b).

In the ultrasonic control unit 3, the transmitting timings Ttimn and the receiving timings Trimn of the respective ultrasonic elements are calculated to focus the ultrasonic waves on the respective ultrasonic focus points on the basis of the input conditions (Step c). Here, Tt designates a transmitter delay time; Tr denotes a receiver delay time; i denotes the element number (A, B, C, ...); and mn denotes two-dimensional coordinates.

Ultrasonic control signals required for operating the elements A, B, C and D of the transmitter element array and the elements O, P, Q and R of the receiver element array are transmitted from the ultrasonic control unit 3 to the transmitter element control unit 7 and the reception signal processing unit 8 through the I/O 5 (Step d). The transmitter element control signals (focus point Fmn, initial value F11) amplified by the transmitter-side amplifiers 11 are supplied to the elements A, B, C and D of the transmitter element array 15 respectively (Step e).

Ultrasonic waves 16 (spherical waves) radiated from the elements A, B, C and D of the transmitter element array 15 respectively are focused on the position of a focus point 17 (Fmn) inside the inspection-target material 21 due to a time difference between the ultrasonic waves 16 (Step f). In FIG. 1, in order to focus the ultrasonic waves 16 on the focus point 17 (Fmn), a transmission signal to the element A present near the outermost portion of the sensor 14 farthest from the focus point 17 (Fmn) is input earliest so that the ultrasonic wave from the element A is radiated earliest. On the contrary, a transmission signal to the element D present near the center of the sensor 14 closest to from the focus point 17 (Fmn) is input latest so that the ultrasonic wave 16 from the element D is radiated latest.

Figure 3:
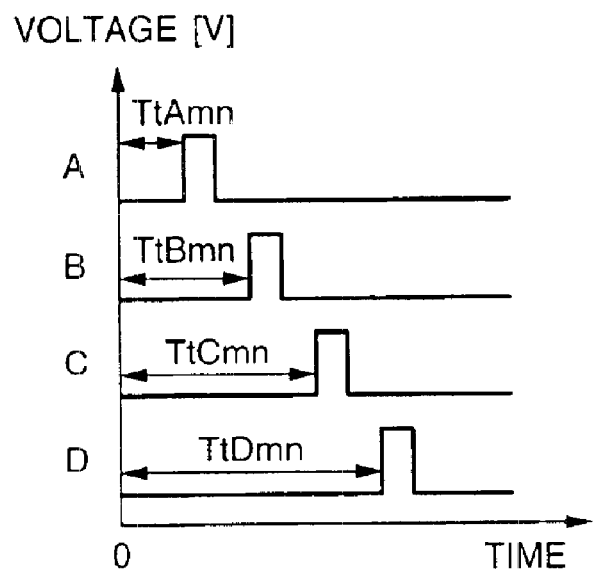
FIG. 3 is a timing chart of transmitter element control signals to respective transmitter elements.
Figure 4:
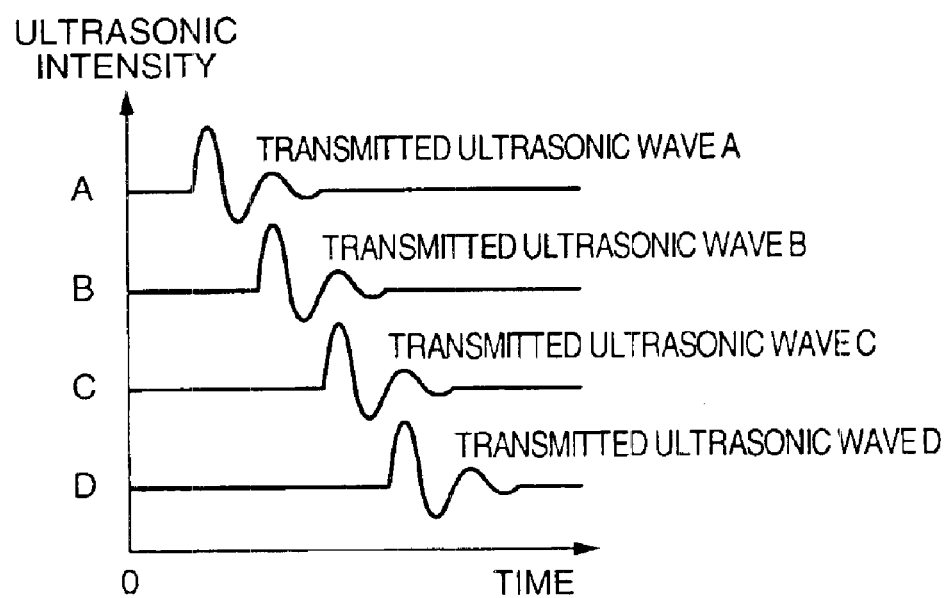
FIG. 4 is a timing chart of generating ultrasonic waves to be transmitted.

FIG. 3 shows a timing chart of the transmitter element control signals to the respective elements. In addition, FIG. 4 shows a generating timing chart of the ultrasonic waves 16 generated in response to the transmitter element control signals in FIG. 3. As described above, the delay times TrAmn, TrBAmn, TrCmn, ... to the respective elements A, B, C and D for focusing the ultrasonic waves on the position of the focus point 17 (Fmn) inside the inspection-target material 21 are calculated by the ultrasonic control unit 3. Thus, the ultrasonic waves can be focused on the position of the focus point 17 (Fmn) inside the inspection-target material 21 due to a time difference among the ultrasonic waves 16 (spherical waves).

When there is a crack tip portion in the focus point 17 (Fmn), the ultrasonic waves are diffracted on the crack tip portion so as to generate diffraction echoes 18. The diffraction echoes 18 enter the elements O, P, Q and R of the receiver element array 19 with a time difference between the diffraction echoes 18, respectively (Step g).

In FIG. 1, the diffraction echo 18 entering the element O on the receiver side present near the center of the sensor 14 closest to the focus point 17 (Fmn) is the earliest temporally, while the diffraction echo 18 entering the element R on the receiver side present near the outermost portion of the sensor 14 farthest from the focus point 17 (Fmn) is the latest temporally. When the diffraction echo 18 enters each element O, P, Q, R of the receiver element array 19, an ultrasonic reception signal (electric signal) corresponding to the intensity and time of the diffraction echo 18 is induced in each element O, P, Q, R of the receiver element array 19. The ultrasonic reception signals (electric signals) are amplified by the receiver-side amplifiers 12 and supplied to the reception signal processing unit 8 (Step h) (here, the receiver-side amplifiers 12 and the reception signal processing unit 8 may be replaced by each other so that the signals are added and synthesized in the reception signal processing unit 8 and then the synthesized signal is amplified by one receiver-side amplifier 12).

In the reception signal processing unit 8, the receiving timing Trimn for synthesizing the ultrasonic reception signals (electric signals) is controlled on the basis of the relation (distance relation) between the focus point 17 (Fmn)

of reception of each element O, P, Q, R of the receiver element array 19 and the position of each element O, P, Q, R of the receiver element array 19, and then the ultrasonic reception signals (electric signals) are added to create one ultrasonic reception signal (Step i). The receiving timing Trimn is calculated by the ultrasonic control unit 3 so as to have a value allowing the focus point of reception of each element O, P, Q, R of the receiver element array 19 to be focused on the focus point (identical with the focus point 17 (Fmn)) of reception determined based on the input conditions.

Figure 5:
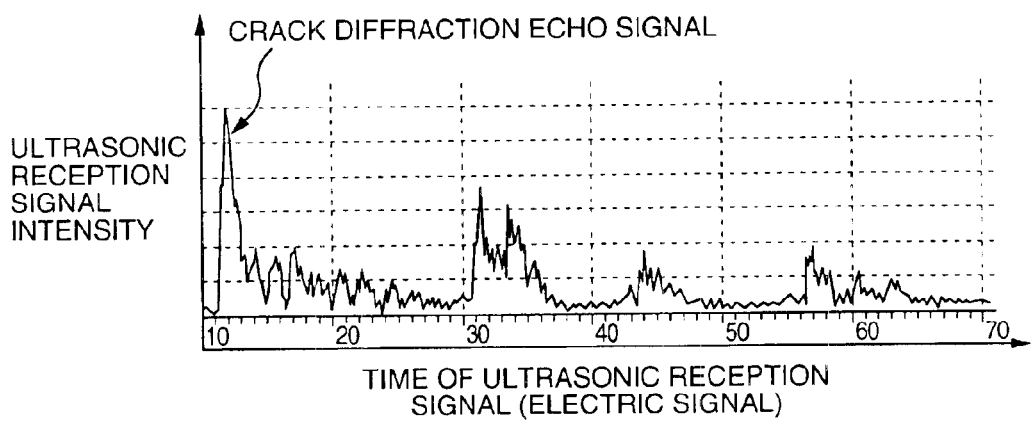
FIG. 5 is a view typically showing Output Display Example 1 (A-scan signal) of a crack signal in the embodiment of the present invention.

The synthesized ultrasonic reception signal is transferred to the information processing unit 4 and the memory 2 through the I/O 5 (Step j). FIG. 5 shows a typical example in which the ultrasonic reception signal obtained thus is processed in accordance with a display mode by the information processing unit 4 and displayed as inspection information on the display unit 6. This signal display is called "A-scan", showing inspection information with the time of the ultrasonic reception signal (electric signal) in the abscissa and the intensity of the ultrasonic reception signal in the ordinate. When a crack diffraction echo signal is displayed as inspection information as shown in FIG. 5, the existence of the crack diffraction echo signal can be recognized as a ground for existence of a crack so that the crack can be detected. In addition, measuring the depth of the crack (crack sizing) can be performed on the basis of the time when the ultrasonic waves are transmitted and the time when the diffraction echoes are detected (propagation time of the ultrasonic waves).

Although the diffraction echoes 18 are faint according to a conventional ultrasonic inspection method, the diffraction echo detectability can be enhanced on a large scale according to the embodiment when the transmitted ultrasonic waves is focused on a crack tip portion and focusing is also performed on the receiver side. In addition, when a range not larger than 30 degrees is used as the transmitting angle of the ultrasonic waves or the receiving angle of the diffraction echoes, the crossing area of their focus points in transmission and reception can be expanded. Thus, robustness can be secured in crack detection and crack sizing. In such a manner, in the embodiment of the present invention, at least one focus point is set in a range where the transmitting/receiving angle of ultrasonic waves will be not larger than 30 degrees. Alternatively, all the focus points may be set in such a range.

Thus, the transmitting timing and the receiving timing of ultrasonic waves are calculated by the ultrasonic control unit 3 so that the focus point of the ultrasonic waves 16 is identical with the focus point of reception thereof. Control signals obtained thus are supplied to the transmitter element control unit 7 and the reception signal processing unit 8 so as to be processed.

When there are a plurality of focus points (F11, F12, . . . Fmn, m=1 to i, and n=1 to j) defined as two-dimensional coordinates, Steps k, l, m, n and o following Step j are executed. Thus, the aforementioned operation from Step e to Step j is performed upon each of the plurality of focus points. Then, finally, in Step p, the reception signal obtained from the received diffraction echoes is processed by the information processing unit 4 in accordance with a desired display mode, and displayed as inspection information in the desired display mode of an image on the display unit 6 by means of the information processing unit, while the information (reception data) of the reception signal is processed and analyzed.

In such a manner, in order to realize an inspection method in a small size with high sensitivity and high resolution and with robustness in crack detection, the embodiment of the present invention may make the following proposals. That is, (1) in the ultrasonic inspection instrument, there is a crossing point (focus point 17) between focused acoustic fields of the transmitter array sensor and the receiver array sensor, and the crossing point between the focused acoustic fields is moved in a range including a point where half the sum of the transmitting angle and the receiving angle of ultrasonic waves with respect to the crossing point between the focused acoustic fields is 30 degrees; (2) the crossing point between the focused acoustic fields is the center between the transmitter array sensor and the receiver array sensor; (3) using an area where the transmitting angle $\theta t$ and the receiving angle $\theta r$ of ultrasonic waves are not larger than 30 degrees, which area has been heretofore regarded as difficult to detect diffraction echoes (the transmitting angle $\theta t$ and the receiving angle $\theta r$ are set to include the area not larger than 30 degrees, respectively), crack inspection and crack sizing tests are performed on the basis of the propagation time of ultrasonic waves transmitted to and received from a crack; (4) the array sensor is made small in size and high in density (element width of 2.0 mm or less and insulator width of 0.2 mm or less) suitably to an array sensor small in size, high in sensitivity and high in resolution; and so on.

Figures 1, 6:
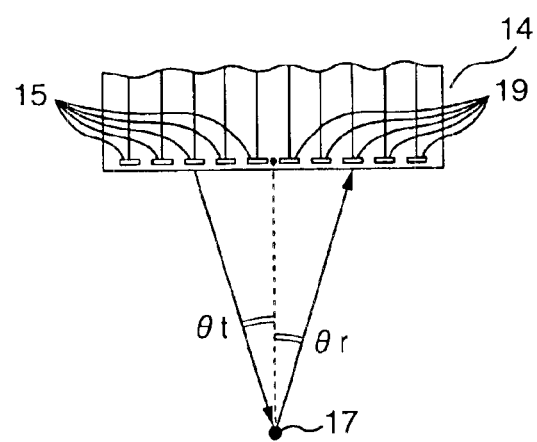
Figures 2, 6:
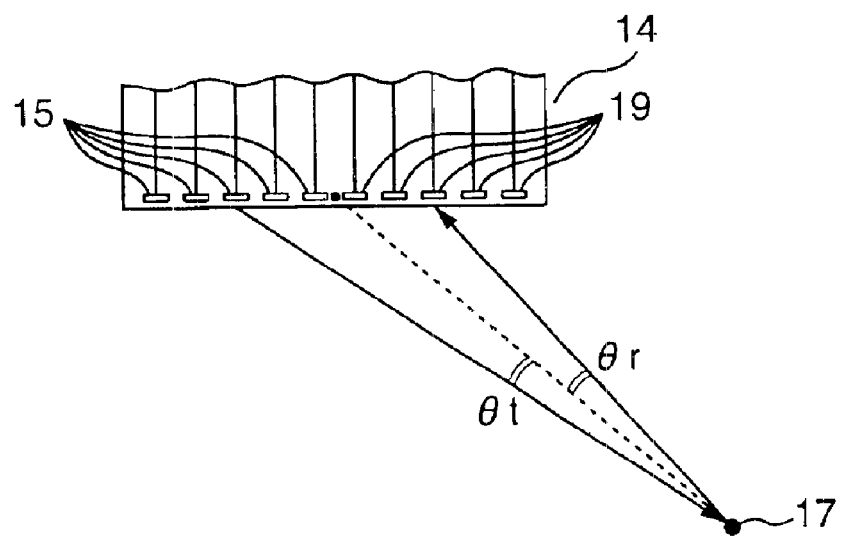

FIGS. 6-1 and 6-2 show the definitions of the transmitting angle $\theta t$ of the ultrasonic waves 16 transmitted from the sensor 14 to the inspection-target material 21 and the receiving angle $\theta r$ of the diffraction echoes 18 that are ultrasonic waves received by the sensor 14. The transmitting angle $\theta t$ is defined as an angle between the line (solid line in FIGS. 6-1 and 6-2) connecting the center of the transmitter element array 15 and the focus point 17 and the line (broken line in FIGS. 6-1 and 6-2) connecting the center of the sensor 14 (between the transmitter element array 15 and the receiver element array 19) and the focus point 17. The receiving angle $\theta r$ is defined as an angle between the line (solid line in FIGS. 6-1 and 6-2) connecting the center of the receiver element array 19 and the focus point 17 and the line (broken line in FIGS. 6-1 and 6-2) connecting the center of the sensor 14 (between the transmitter element array 15 and the receiver element array 19) and the focus point 17.

In the embodiment of the present invention, there is a crossing point (focus point 17) between the focused acoustic field of the ultrasonic waves transmitted by the ultrasonic inspection instrument and the focused acoustic field of the ultrasonic waves received as diffraction echoes by the ultrasonic inspection instrument, and the crossing point between the focused acoustic fields is moved in a range including a point where half the sum of the transmitting angle $\theta t$ and the receiving angle $\theta r$ will be not larger than 30 degrees with respect to the crossing point between the focused acoustic fields. In order to carry out such an operation, transmitted ultrasonic focus points (F11, F12, . . . , Fmn, m=1 to i and n=1 to j) and receiver-side focus points (F11, F12, . . . , Fmn, m=1 to i and n=1 to j) are input as input conditions such that the position of the crossing point between the focused acoustic fields is displaced in a range including a point where each of the transmitting angle $\theta t$ and the receiving angle $\theta r$ will be not larger than 30 degrees. Thus, the operation can be achieved along the operation flow in FIG. 2 and by means of the instrument in FIG. 1.

Figure 7:
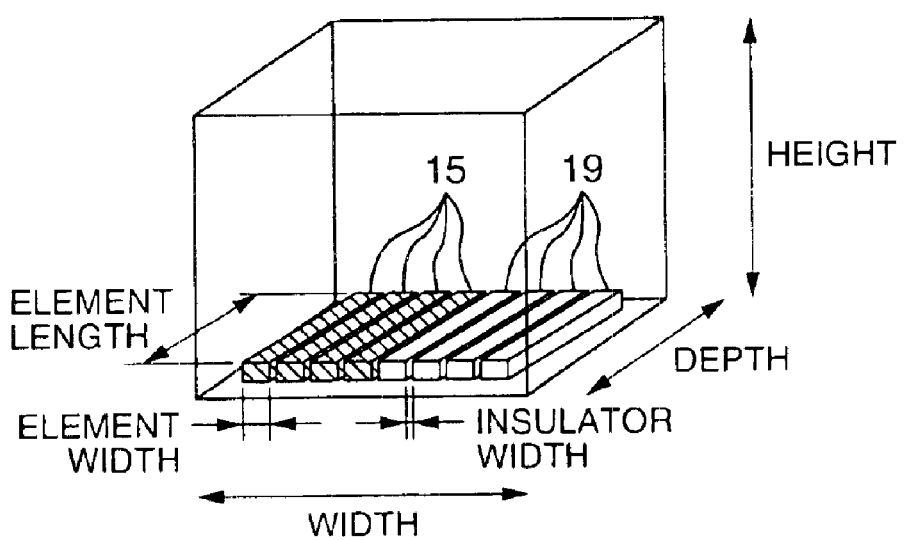
FIG. 7 is an explanatory view of definitions of width, depth and height of an array sensor, width and length of each element and insulator width.

FIG. 7 shows the definitions of the width, depth and height of the sensor 14, the width and length of elements for transducing electric signals into ultrasonic waves, that is, elements constituting the transmitter element array 15 and the receiver element array 19, and insulator width between adjacent ones of the elements.

In the embodiment of the present invention, crack detection or sizing can be performed in the following manner. That is, a sensor 14 in which a transmitter array sensor and a receiver array sensor are integrated compactly is used; the size of the sensor 14 is smaller than or equal to the width of an inspection-target portion or a weld metal as an inspection-target portion; the width of each of the elements constituting the transmitter element array 15 and the receiver element array 19 mounted in the array sensor 14 is not smaller than 2 times and not larger than 40 times as large as the distance between adjacent ones of the elements; and particularly in an ultrasonic inspection instrument for use in a nuclear reactor, the foot print of the array sensor to be brought into direct contact with a weld metal or a base material as a surface to be inspected is made small in dimensions to be not larger than 30 mm in the width direction of the sensor 14 and not larger than 30 mm in the depth direction of the sensor 14, and the sensor 14 is brought into direct contact with a crack of the weld metal from above. When the element width exceeds 2.0 mm, ultrasonic waves radiated just downward from of each of the elements of the sensor 14 are intensified in the just downward direction while ultrasonic waves radiated transversely from of each of the elements of the sensor 14 are weakened. As a result, it becomes difficult to perform control over focusing of the ultrasonic waves. On the contrary, when the element width is smaller than 0.1 mm, the energy of transmissible ultrasonic waves is weakened. Thus, it becomes difficult to allow the ultrasonic waves to propagate to a deep position. In consideration of such conditions, the element width is set to be in a range of from 0.1 mm to 2.0 mm, and the interelement insulator width is set to be in a range of from 0.05 mm to 0.2 mm. The sensor 14 small in size and high in element density is arranged in such a manner.

For example, the sensor 14 was arranged in the form of an array probe as follows. That is, as for the element width and the interelement insulator width of the sensor 14, the interval between elements (ultrasonic transducers) of the transmitter element array 15 and the receiver element array 19 was set at 1.0 mm (element width: 0.8 mm and insulator width: 0.2 mm), and an array probe having 16 elements in total of 8 elements in the transmitter element array 15 and 8 elements in the receiver element array 19 was formed to have a width of 16 mm (=1.0 mm/element×16 elements) and an element length of 10 mm. In addition, the sensor 14 was arranged in the form of another array probe as follows. That is, the interval between elements (ultrasonic transducers) of the transmitter element array 15 and the receiver element array 19 was set at 0.5 mm (element width: 0.4 mm and insulator width: 0.1 mm), and an array probe having 32 elements in total of 16 elements in the transmitter element array 15 and 16 elements in the receiver element array 19 was formed to have a width of 16 mm (=0.5 mm/element×32 elements) and an element length of 10 mm. Further, the sensor 14 was arranged in the form of a further array probe as follows. That is, the interval between elements (ultrasonic transducers) of the transmitter element array 15 and the receiver element array 19 was set at 0.25 mm (element width: 0.2 mm and insulator width: 0.05 mm), and an array probe having 64 elements in total of 32 elements in the transmitter element array 15 and 32 elements in the receiver element array 19 was formed to have a width of 16 mm (=0.25 mm/element× 64 elements) and an element length of 10 mm. Thus, the sensor 14 can be arranged so that its section (foot print) defined by the width and depth of the sensor 14 is very small to be about 16 mm in the width direction by 10 mm in the depth direction.

That is, in the embodiment of the present invention, crack inspection and crack sizing can be achieved by use of the small-size sensor 14 having a very small sectional area (foot print) measuring 30 mm or less in width direction by 30 mm or less in depth direction. The width of a typical weld metal inside a nuclear reactor is about 20–50 mm. In consideration of contact on such a weld metal, inspection can be carried out satisfactorily when the foot print of the sensor 14 is made not larger than 30 mm in the width direction and not larger than 30 mm in the depth direction.

In the aforementioned description, an expression "the foot print of the array sensor to be brought into direct contact with a weld metal or a base material as a surface to be inspected is made small in dimensions to be not larger than 30 mm by 30 mm." is used. However, this expression also implies that partial immersion (water distance not deeper than 10 mm) used for avoiding friction against the surface of the inspection-target material may be carried out besides the method for bringing the sensor 14 into direct contact with the surface of the material to be inspected.

Figure 8:
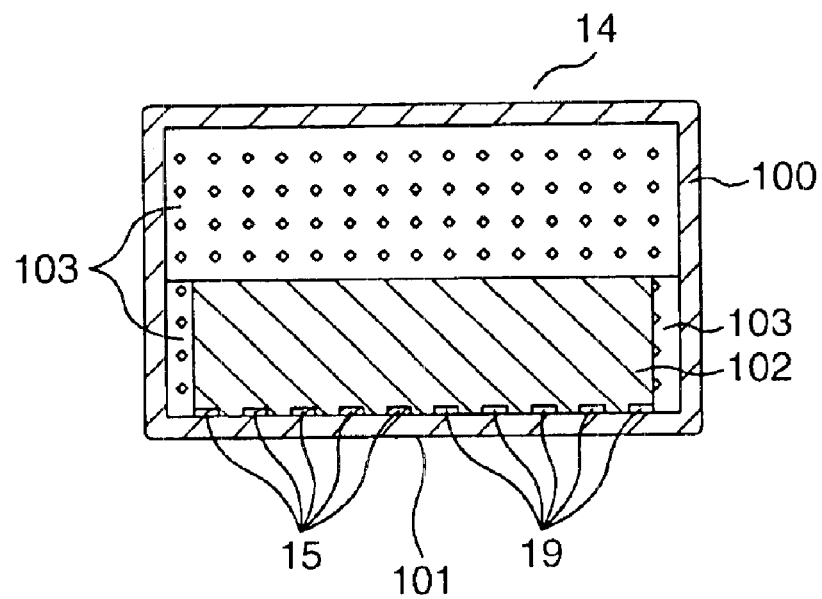
FIG. 8 is a diagram of a structure of the array sensor.
Figure 9:
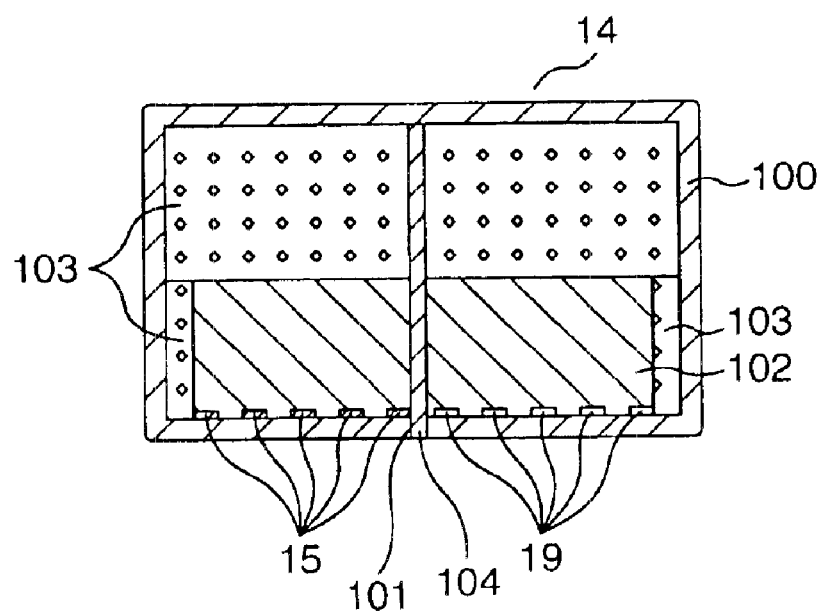
FIG. 9 is a diagram of another structure of the array sensor.

FIG. 8 shows an example of the structure of the sensor 14. The elements of the transmitter element array 15 and the receiver element array 19 are placed on an epoxy resin plate 101 and fixed in position by resin 102. The epoxy resin plate 101 is an entrance/exit surface through which ultrasonic waves will income and outgo. A sound insulator 103 for absorbing ultrasonic waves is charged between a casing 100 and the resin 102. In another example of the structure of the sensor 14 shown in FIG. 9, the elements of the transmitter element array 15 and the receiver element array 19 are placed on an epoxy resin plate 101 and a sound absorbing material 104 (cork material or the like) is placed between the transmitter element array 15 and the receiver element array 19. Thus, acoustic crosstalk between the transmitter element array 15 and the receiver element array 19 can be reduced on a large scale so that reduction in noise and further improvement in detectability can be attained.

Figure 10:
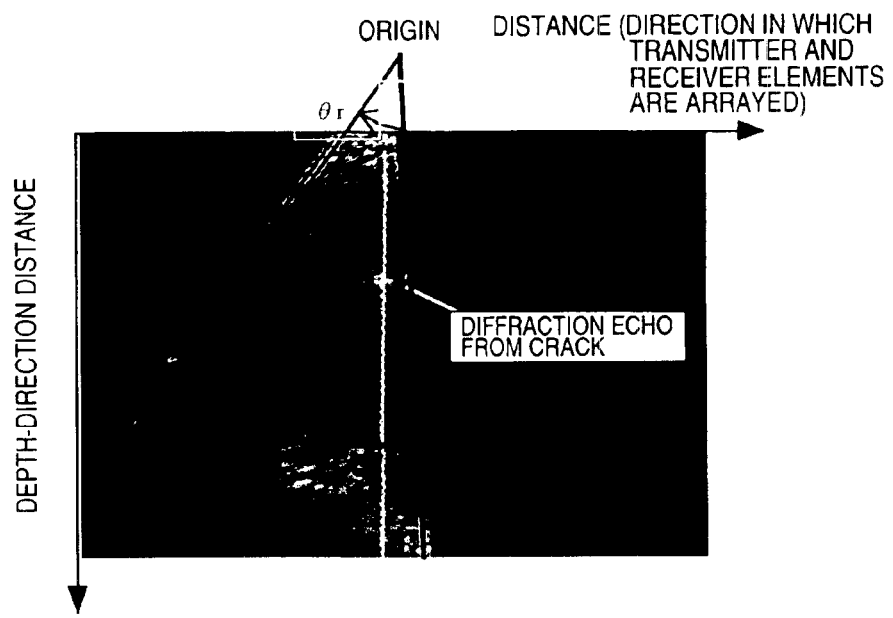
FIG. 10 is a view of Output Display Example 2 of a crack signal according to the present invention, showing paper on which an image displayed on a display unit of the ultrasonic inspection instrument has been printed by a printer.

As will be described later in detail in another embodiment, according to this instrument configuration, it is possible to electronically scan the focus point 17 just under the center of the sensor 14, that is, to move the position of the focus point 17. FIG. 10 shows a typical example of a crack signal obtained as inspection information and displayed on the display unit 6. The signal display shows the crack depth with the abscissa designating the distance in the direction in which the transmitter element array 15 and the receiver element array 19 are arrayed in the array sensor 14 and with the ordinate designating the distance in the direction toward the bottom of the sensor 14. The origin in FIG. 10 is the center of the receiver array probe, showing the signal intensity (signal intensity in A-scan being displayed in a color shaded image) at the time of the receiving angle θr. That is, the shading distribution on the two-dimensional coordinates shows the ultrasonic reception signal (electric signal) intensity. It can be estimated that a tip of a crack as a generation (reflection) source of ultrasonic waves is present in the portion where the ultrasonic reception signal (electric signal) intensity is high. Thus, crack sizing can be achieved. As is observed in FIG. 10, the tip of the crack can be recognized visually so that the objectivity of crack detection and crack sizing can be improved.

Figure 11:
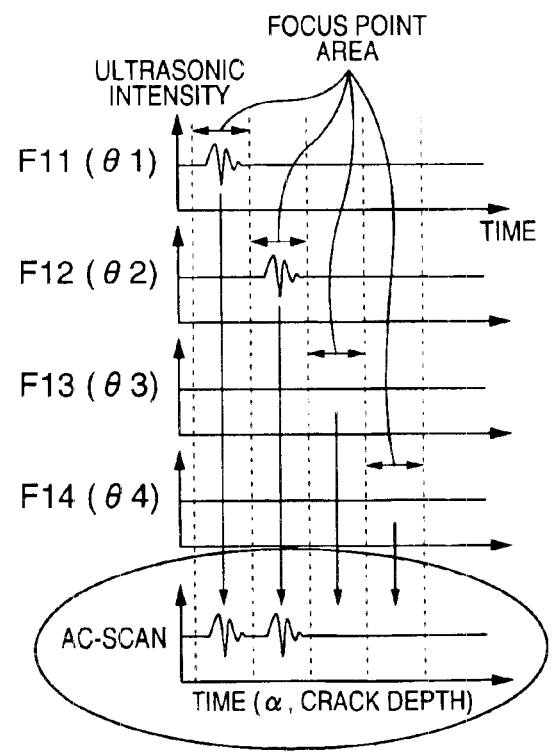
FIG. 11 is a view typically showing Output Display Example 3 of a crack signal according to the present invention.

FIG. 11 shows another display example of the ultrasonic inspection instrument according to the embodiment of the present invention. FIG. 11 shows an example in the case where there are two crack tips. A-scan is displayed for each θr as to the focus point depth F11 (θr=θ1), F12 (θr=θ2), F13 (θr=θ3), F14 (θr=θ4), . . . FIG. 11 shows schematic waveforms of the A-scan in F11 (θr=θ1), F12 (θr=θ2), F13 (θr=θ3) and F14 (θr=θ4) on this occasion. In view of F11 (θr=θ1), an ultrasonic signal present in the ultrasonic focus point area is regarded as a crack indication signal. Similarly, in view of the ultrasonic focus point areas of F12 (θr=θ2), F13 (θr=θ3) and F14 (θr=θ4), gates are applied to the ultrasonic focus point areas to add all the ultrasonic signals in the ultrasonic focus point areas. Thus, an A-scan waveform (AC-scan) is obtained as shown in the lowest portion of FIG. 11. A crack tip can be regarded as being present in the place where an ultrasonic signal exists in the AC-scan. In such a manner, crack detection and crack sizing can be achieved.

Figure 12:
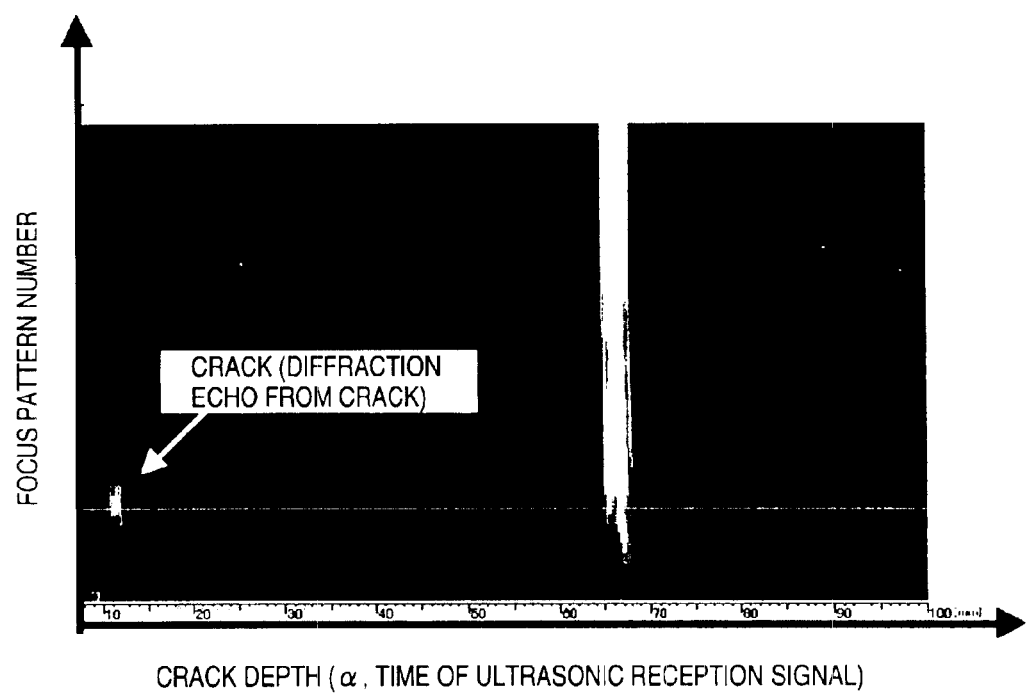
FIG. 12 is a view of Output Display Example 4 of a crack signal according to the present invention, showing paper on which an image displayed on the display unit of the ultrasonic inspection instrument has been printed by a printer.

FIG. 12 shows another display example of inspection information according to the embodiment of the present invention. This signal display of inspection information is aimed at objective estimation of crack depth. The abscissa designates the crack depth (α, time of ultrasonic reception signal) and the ordinate designates the focus pattern number. The focus pattern number in the ordinate is a transmitted ultrasonic focus point (=receiver-side focus point) number corresponding to F11, F12, F13 or F14. That is, in FIG. 12, the signal intensity of A-scan corresponding to the ordinate (focus pattern number) is displayed as a color shaded image. It can be estimated that a crack tip as a source of generation (reflection) of ultrasonic waves that are diffraction echoes exists in a portion where the intensity of the ultrasonic reception signal (electric signal) is high. Thus, crack sizing can be achieved. As is observed from FIG. 12, the crack tip can be recognized visually so that objectivity in crack detection and crack sizing can be improved.

Figure 13:
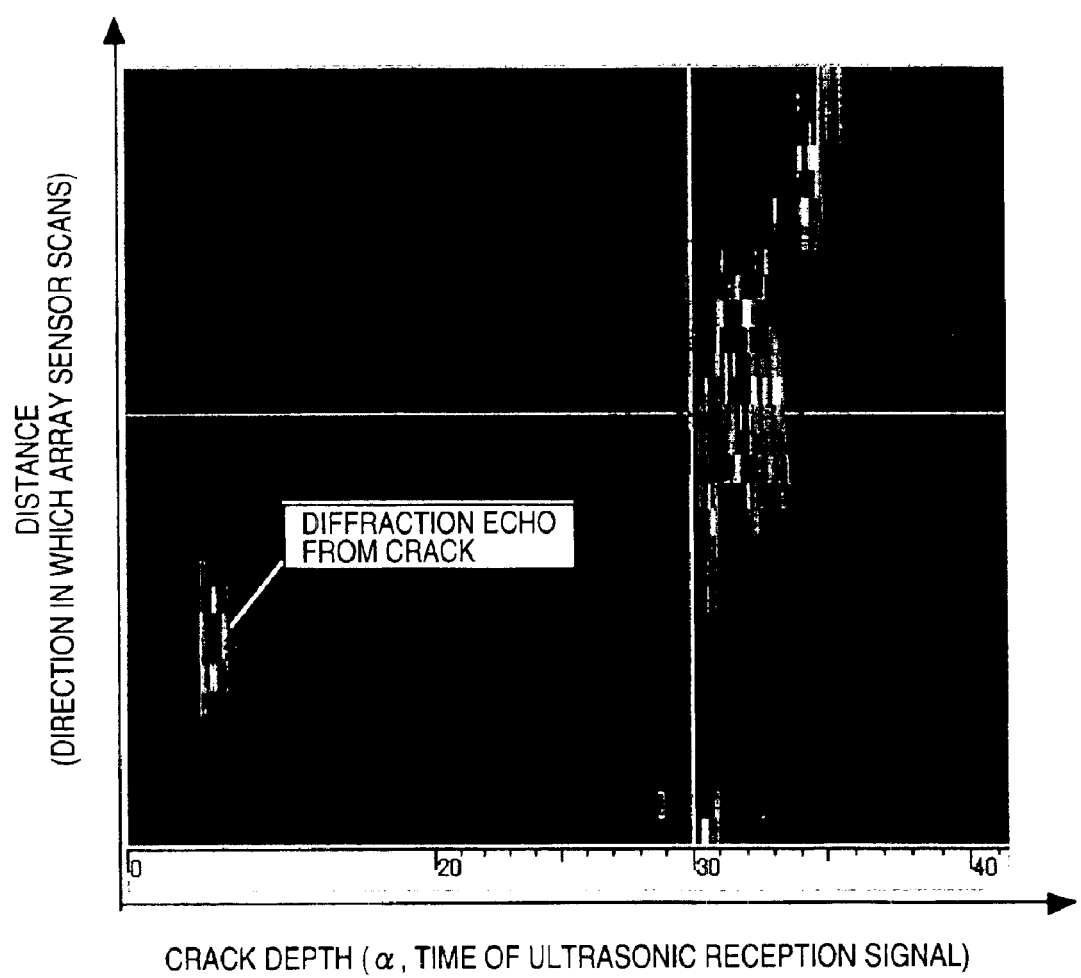
FIG. 13 is a view of Output Display Example 5 of a crack signal according to the present invention, showing paper on which an image displayed on the display unit of the ultrasonic inspection instrument has been printed by a printer.

Assume that the sensor 14 is moved mechanically (in a horizontal direction perpendicular to the direction in which the respective elements of the transmitter element array 15 and the receiver element array 19 of the sensor 14 are arrayed) in the inspection conditions in which each focus point 17 is scanned electronically just under the center of the sensor 14. FIG. 13 shows a typical example of inspection information including a crack signal displayed on the display unit 6 in such a case. The abscissa designates the time of the ultrasonic reception signal (electric signal) and the ordinate designates the distance in the scanning direction of the sensor 14. The shading distribution on this two-dimensional coordinates expresses the intensity of the ultrasonic reception signal (electric signal). That is, it can be estimated that a crack tip as a source of generation (reflection) of ultrasonic waves that are diffraction echoes exists in the portion where the intensity of the ultrasonic reception signal (electric signal) is high locally. In addition, it can be concluded that another portion where the intensity is high stationarily involves in a bottom echo. Thus, detection and sizing of a crack can be achieved.

The information of the reception signal obtained by transmitting and receiving ultrasonic waves is visualized on the display unit 6 as inspection information based on any one of the displays shown in FIGS. 10 to 13. Any inspection information is obtained by processing in the information processing unit 4 based on reception signals sent from the reception signal processing unit 8 to the memory 2 and accumulated therein or the reception signal sent to the information processing unit 4, and then displayed on the display unit 6.

When the position of the lower tip of the crack 22 is roughly known in FIG. 1, the input conditions are set to assign the focus point 17 of the ultrasonic waves 16 to one location corresponding to the position of the tip. The focus point 17 of the ultrasonic waves 16 is set at the tip of the crack 22 (the lower tip of the crack 22 in FIG. 1) opened in the surface of the inspection-target material 21. The ultrasonic waves 16 are transmitted from the elements A, B, C and D of the transmitter element array 15 toward the focus point 17 so as to be focused on the focus point 17. Thus, the ultrasonic waves 16 are focused on the focus point 17 corresponding to the tip of the crack 22. The focused ultrasonic waves 16 are diffracted on the tip of the crack 22 so as to generate diffraction echoes 18. The diffraction echoes 18 enter the elements O, P, Q and R of the receiver element array 19 and are received by the elements O, P, Q and R of the receiver element array 19. In response to the diffraction echoes received by the elements O, P, Q and R respectively, ultrasonic reception signals (electric signals) are outputted from the elements O, P, Q and R respectively, and transferred to the transmission/reception signal delay control unit 7. After amplification and delay processing is performed on the ultrasonic reception signals, the waveform shown in FIG. 5, which is an ultrasonic waveform, is displayed on the display unit 6. The display may include contents as shown in FIGS. 10, 11, 13 or the like. Thus, crack detection and crack sizing can be achieved. Description of FIG. 1 has been made on a manner when a tip of the crack 22 is known to some extent. In this case, since the number of focus points 17 is one, it is not necessary to set a plurality of focus points 17 and move the focus point from one to another.

Figure 14:
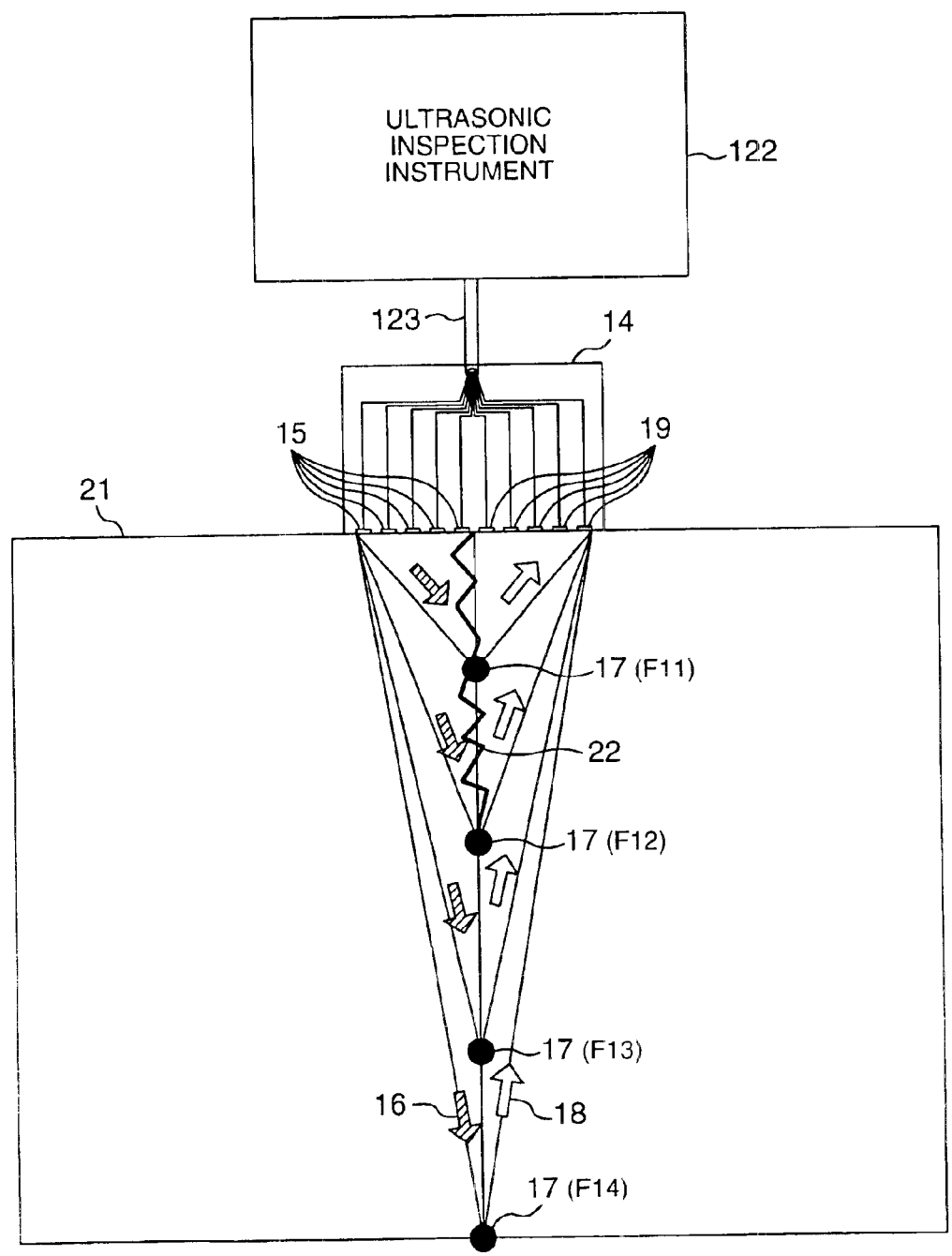
FIG. 14 is a view showing an example of the ultrasonic inspection instrument according to the present invention applied to crack detection and crack sizing.

FIG. 14 shows another example in which the ultrasonic inspection instrument according to the embodiment of the present invention is applied to crack detection and crack sizing. The manner when the lower tip of the crack 22 was known to some extent was described above. In actual inspection, however, only initial information that an opening of the crack 22 is present in the surface of the inspection-target material 21 can be often obtained by visual inspection with a camera or the like. That is, an ultrasonic inspection test is often performed in the state where the depth of the crack 22, that is, the position of the lower tip of the crack 22 is not known. FIG. 14 shows an example in which an ultrasonic inspection test is performed in such a state that the depth of the crack 22 is not known. Description will be made below in detail.

The procedure of crack inspection and sizing will be described below with reference to FIG. 14. The sensor 14 is pressed just above the crack 22 generated in the inspection-target material 21, that is, onto the opening of the crack 22 appearing in the surface of the inspection-target material 21 so that the central portion of the sensor 14 faces the opening.

The alignment of the crack 22 and the sensor 14 is performed by visual observation or by remote visual observation using a camera and an illumination, so that the center of the sensor 14 is aligned with the opening of the crack 22. That is, crack detection and crack sizing are performed with the sensor 14 positioned just above the crack 22.

The depth of the crack 22 cannot be known by visual observation from the opening side of the crack 22 present in the surface of the inspection-target material. Therefore, according to this embodiment, the focus point 17 of the transmitted ultrasonic waves 16 (=focus point from which the ultrasonic waves are received) is moved continuously or discretely in the just underneath direction of the sensor 14 which is the depth direction of the crack. This scanning of the focus point 17 of the transmitted ultrasonic waves 16 (=focus point from which the ultrasonic waves are received) in the underneath direction of the sensor 14 can be performed under the control of the transmitter element control unit 7 and the reception signal processing unit 8 by the ultrasonic control unit 3. Since the ultrasonic waves have a finite focus width of about several millimeters, diffraction echoes 18 occur due to interaction between the tip portion of the crack 22 and the focused transmitted ultrasonic waves 16. The diffraction echoes 18 enter the receiver element array 19. Ultrasonic reception signals (electric signals) generated thus are amplified by the receiver-side amplifiers 12, and transferred to the reception signal processing unit 8 so as to be synthesized. The synthesized signal is stored into the memory 2 or processed by the information processing unit 4. Thus, here, an ultrasonic waveform is obtained as shown in FIG. 5, and an output of crack detection and crack sizing is obtained as shown in FIG. 10 or 13. As a result, crack detection and crack sizing can be achieved even if the depth of the crack 22 is not known.

An example in which the gains of the transmitter-side amplifiers are changed in accordance with the position (depth) of the focus point 17 will be described with reference to FIG. 14 and Table 1. In FIG. 14, the focus point 17 is moved from F11 to F14 through F12 and F13. To this end, in the example of FIG. 14, four focus points 17 for transmission and reception are set as input conditions for determining an ultrasonic transmitting/receiving pattern.

The ultrasonic propagation distance to the vicinity of the internal surface layer (F11) of the focus points 17 in the inspection-target material 21 is shorter than that to a deep point (F14) so that the ultrasonic attenuation inside the inspection-target material 21 in the vicinity of the surface layer (F11) is lower than that at the deep point (F14). Hence, the ultrasonic intensity in the vicinity of the surface layer (F11) is high. On the contrary, the ultrasonic propagation distance to the deep point (F14) of the focus points is long so that the ultrasonic attenuation inside the inspection-target material 21 at the deep point (F14) of the focus points is high. Hence, the ultrasonic intensity at the deep point (F14) of the focus points becomes lower than that in the vicinity of the surface layer (F11). If the gains of the transmitter-side amplifiers 11 are set based on the deep point (F14) of the focus points, the gains will be excessively high in the vicinity of the surface layer (F11) so that an ultrasonic dead band will be expanded. Thus, a crack in the vicinity of the surface layer (F11) of the inspection-target material 21 cannot be detected.

For this reason, the gains of the transmitter-side amplifiers are set to be lower in the vicinity of the surface layer (F11) of the inspection-target material 21 than in the deep point (F14) of the focus points. That is, according to this embodiment, in order to provide ultrasonic intensity optimal for the focus point depth, the ultrasonic intensity optimal for the focus point depth is calculated and set by the ultrasonic control unit 3, and the transmitter-side amplifier control unit 9 is controlled through the I/O 5 to change the gains of the transmitter-side amplifiers 11 in accordance with the focus point depth. Accordingly, the ultrasonic control unit 3 and the transmitter-side amplifier control unit 9 also function as a first amplification control unit. Thus, crack detection and crack sizing can be achieved over a wide range from the vicinity of the internal surface layer (F11) of the focus points 17 to the deep point (F14) of the focus points in the inspection-target material 21.

TABLE 1

Example of Setting Gains of Transmitter-side amplifiers

| focus point | | AT1 | AT2 | AT3 | AT4 |
|---|---|---|---|---|---|
| shallow | F11 | GA1 | GA2 | GA3 | GA4 |
| ↓ | F12 | GB1 | GB2 | GB3 | GB4 |
| deep | F13 | GC1 | GC2 | GC3 | GC4 |
|  | F14 | GD1 | GD2 | GD3 | GD4 |

GA < GB < GC < GD

Table 1 shows typical setting of the gains of the transmitter-side amplifiers 11. AT1 to AT4 designate the amplifier names of the transmitter-side amplifiers 11 respectively, with each amplifier connected to its corresponding element. F11 to F14 designate the focus points 17 for transmission and reception, in order of increasing depth of the focus points 17. The gain of each amplifier AT1 to AT4 at a focus point (F11 to F14) is G. For example, the gain of the amplifier AT1 at the focus point F11 is GA1, and the gain of the amplifier AT1 at the focus point F14 is GD1. As shown in Table 1, the gain of each amplifier is characterized in that the gain is optimized in accordance with the depth of the focus point, and set to increase in proportion to the depth of the focus point (GA<GB<GC<GD).

Although an example of the embodiment in which the gain of each transmitter-side amplifier is changed in accordance with the depth of the focus point 17 has been described above, such an effect can be attained even when the gain of each receiver-side amplifier 12 is changed in accordance with the depth of the focus point 17. Such an example will be described below. The ultrasonic propagation distance to the vicinity of the surface layer (F11) of the inspection-target material 21 is shorter than that to the deep point (F14) so that the ultrasonic attenuation inside the inspection-target material 21 in the vicinity of the surface layer (F11) is lower than that at the deep point (F14). Hence, the ultrasonic intensity in the vicinity of the surface layer (F11) is high. On the contrary, the ultrasonic propagation distance to the deep point (F14) of the focus points is long so that the ultrasonic attenuation inside the inspection-target material 21 at the deep point (F14) of the focus points is high. Hence, the ultrasonic intensity at the deep point (F14) of the focus points becomes lower than that in the vicinity of the surface layer (F11). If the gain of each receiver-side amplifier 12 is set in accordance with the deep point (F14) of the focus points, the gain will be too high in the vicinity of the surface layer (F11) to detect a crack in the vicinity of the surface layer (F11) of the inspection-target material 21 correctly.

For this reason, the gains of the receiver-side amplifiers 12 are set to be lower in the vicinity of the surface layer (F11) of the inspection-target material 21 than at the deep point (F14) of the focus points. That is, the present invention is characterized in that, in order to provide ultrasonic detectability optimal for the focus point depth, the ultrasonic detectability optimal for the focus point depth is calculated and the gains of the receiver-side amplifier 12 are set by the ultrasonic control unit 3, and the receiver-side amplifier control unit 10 is controlled through the I/O 5 to change the gains of the receiver-side amplifiers 12 in accordance with the focus point depth. Accordingly, the ultrasonic control unit 3 and the receiver-side amplifier control unit 10 also function as a second amplification control unit.

Thus, crack detection can be achieved over a range from the vicinity of the surface layer (F11) to the deep point (F14)

of the focus points in the inspection-target material 21. Table 2 shows typical setting of the gains of the receiver-side amplifiers 12. AR1 to AR4 designate the amplifier names of the receiver-side amplifiers 12 respectively, with each receiver-side amplifier 12 connected to its corresponding element of the receiver element array. F11 to F14 designate the focus points 17 in order of increasing depth of the focus points 17. The gain of each amplifier (AR1 to AR4) at a focus point (F11 to F14) is G. For example, the gain of the amplifier AR1 at the focus point F11 is GO1, and the gain of the amplifier AR1 at the focus point F14 is GR1. As shown in Table 2, the gain of each amplifier is optimized in accordance with the depth of the focus point, and set to increase in proportion to the depth of the focus point (GO<GP<GQ<GR).

TABLE 2

Example of Setting Gains of Receiver-side amplifiers

| focus point | | AR1 | AR2 | AR3 | AR4 |
|---|---|---|---|---|---|
| shallow | F11 | GO1 | GO2 | GO3 | GO4 |
| ↓ | F12 | GP1 | GP2 | GP3 | GP4 |
| deep | F13 | GQ1 | GQ2 | GQ3 | GQ4 |
| | F14 | GR1 | GR2 | GR3 | GR4 |

GO < GP < GQ < GR

Although an example in which the gains of the transmitter-side amplifiers or the receiver-side amplifiers are changed in accordance with the depth of the focus point has been described above, such an effect can be obtained also by changing the gains of both the transmitter-side amplifiers and the receiver-side amplifiers in accordance with the focus point (depth). That is, this case is characterized in that the gain of each amplifier of both the transmitter-side amplifiers and the receiver-side amplifiers is optimized in accordance with the depth of the focus point 17, and set to increase in proportion to the depth of the focus point 17.

Figure 15:
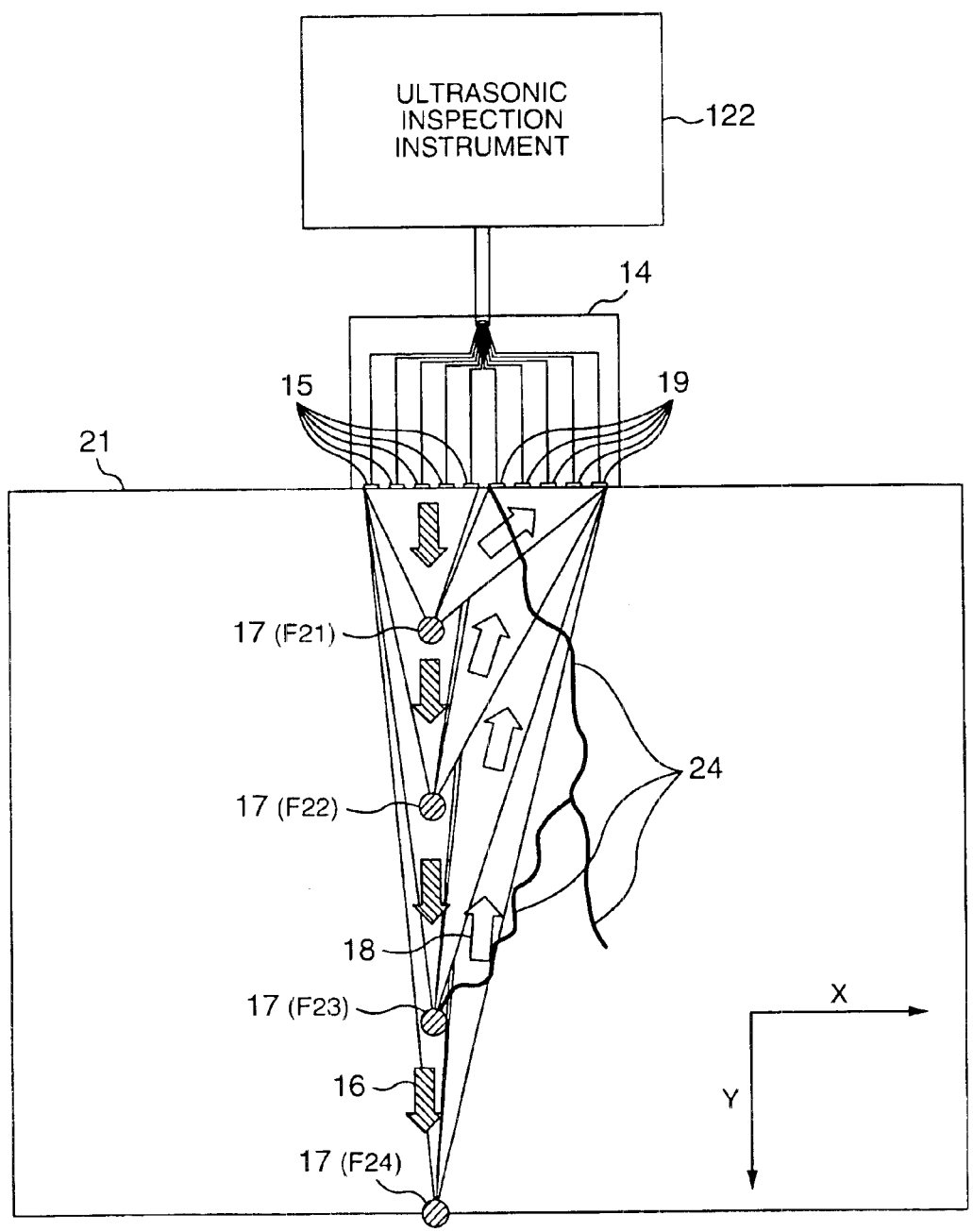
FIG. 15 is a view showing another example of the ultrasonic inspection instrument according to the present invention applied to crack detection and crack sizing.

FIG. 15 shows another example in which the ultrasonic inspection instrument according to the embodiment of the present invention is applied to crack detection and crack sizing. As described above, the example of FIG. 14 has showed a crack detection and crack sizing method in the case where a crack 22 had developed just under the sensor 14.

Although it can be considered that the crack 22 often develops right under the sensor 14 as shown in FIG. 14, it is also necessary to consider the case, as a rare case, where the crack 22 develops not right under the sensor 14 but obliquely to the sensor 14 or a tip of the crack branches. FIG. 15 shows an example in which an ultrasonic inspection test is carried out when the developed shape of a crack is not known. Description will be made below in detail on the example. The procedure of crack inspection and sizing will be described below. The sensor 14 is pressed just above the surface opening portion of a crack 24 appearing in the inspection-target material 21 and developing obliquely or branching at the crack tip. Since the developing direction of the crack or the shape of the crack is not known by visual observation from the surface opening side, scanning is first performed while moving the focus point of the transmitter ultrasonic waves 16 (=focus point from which the ultrasonic waves are received) continuously or discretely in the underneath direction of the sensor 14, so as to collect ultrasonic data. Next, the focus point (=focus point from which the ultrasonic waves are received) is moved by a distance about ½ or ¼ of the ultrasonic focus width (about several millimeters) in the element array direction (X-direction in FIG. 15) of the transmitter element array 15 of the sensor 14. Then, scanning is performed while moving the focus point continuously or discretely in the underneath direction (Y-direction in FIG. 15), so as to collect ultrasonic data.

After that, the focus point (=focus point from which the ultrasonic waves are received) is moved by a distance about ½ or ¼ of the ultrasonic focus width (about several millimeters) in the element array direction (X-direction in FIG. 15) of the transmitter element array 15 of the sensor 14. Then, scanning is performed while moving the focus point continuously or discretely in the underneath direction (Y-direction in FIG. 15), so as to collect ultrasonic data. When such a procedure is repeated, two-dimensional scanning over a range under the sensor 14 can be achieved. By the scanning method and the crack detection according to this embodiment, crack detection and crack sizing can be performed even upon the crack 24 appearing in the inspection-target material 21 and developing obliquely or branching at the crack tip.

Figure 16:
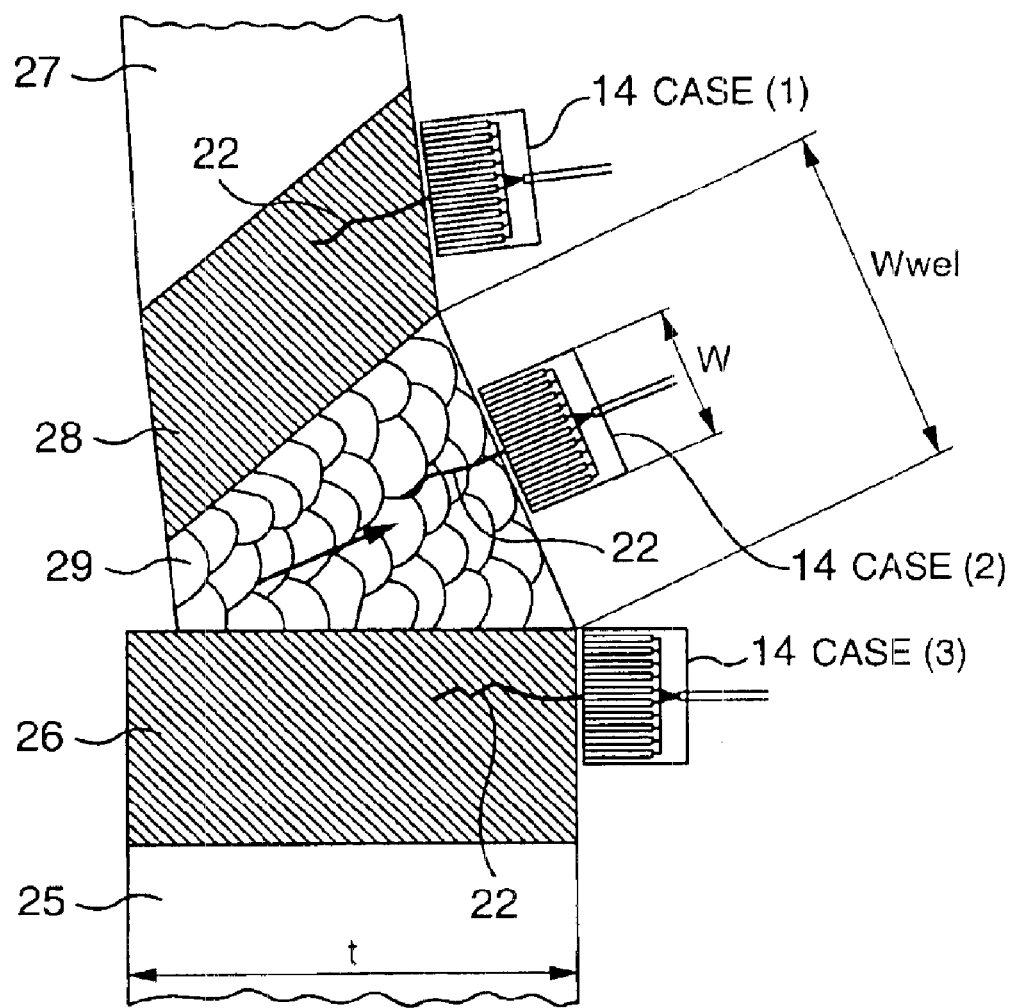
FIG. 16 is a view showing each case in which an array sensor according to the present invention is applied to a shroud support portion in a nuclear reactor.

FIG. 16 shows an example in which the ultrasonic inspection instrument according to any one of the aforementioned embodiments is applied to the operation for ultrasonic inspection of a shroud support portion in a nuclear reactor. A shroud support 25 and a shroud support ring 27 in the nuclear reactor are mounted in a pressure vessel, and welded with each other by an inconel weld metal 29. Temperature rise occurs when the inconel weld metal 29 for connecting the shroud support 25 and the shroud support ring 27 is obtained by welding. The temperature rise generates a heat affected zone 28 of the shroud support ring near the inconel weld metal 29. Similarly, the temperature rise generates a heat affected zone 26 of the shroud support near the inconel weld metal 29. Generally, the inconel weld metal 29, the heat affected zone 28 of the shroud support ring and the heat affected zone 26 of the shroud support are regarded as high in sensitivity to Stress Corrosion Cracking. Thus, crack detection and crack sizing over the metal and zones are very significant problems to be solved. Crack detection and crack sizing over the near surface crack 22 are very difficult according to any conventional ultrasonic inspection method using angle probes.

Figure 17:
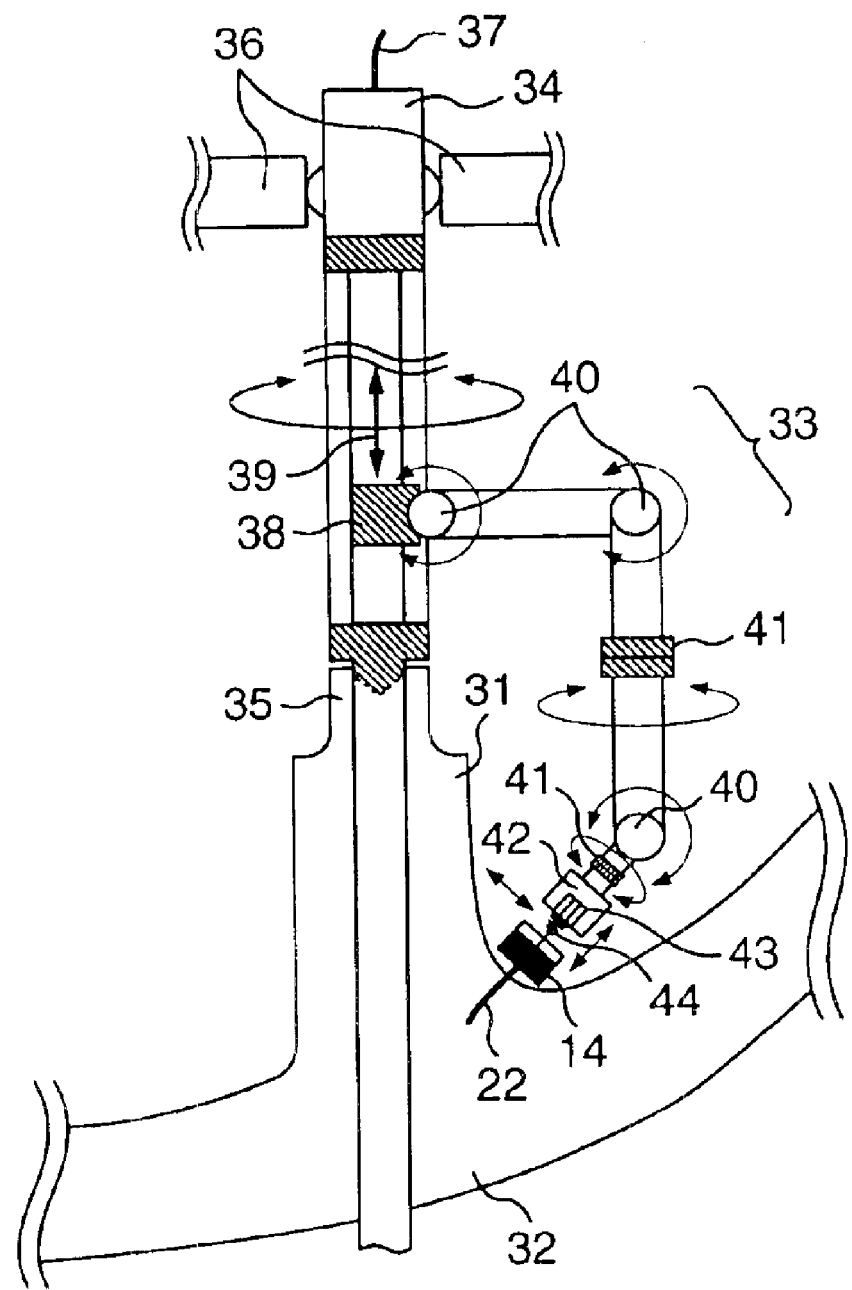
FIG. 17 is a view showing a case in which the present invention is applied to the vicinities of CRD stub tubes and a pressure vessel in a core bottom portion of a nuclear reactor.

Inspection of a weld portion using a conventional TOFD technique is performed to cut across its weld line. Therefore, any ultrasonic beam follows a propagation course from a transmitter probe to a receiver probe through a base material, a weld metal and the base material again. It is known that the ultrasonic beam is redirected when the ultrasonic beam enters the weld metal from the base material, and the ultrasonic beam is diffused/attenuated inside the weld metal. In addition, according to an ultrasonic inspection method using a conventional TOFD technique, it is necessary to perform scanning while fixing a transmitter probe and a receiver probe at a fixed distance. Thus, the external dimensions of the instrument becomes so large that the instrument cannot be applied to the inconel weld metal 29, the heat affected zone 28 of the shroud support ring and the heat affected zone 26 of the shroud support, which have a narrow width and a step as shown in FIG. 17. FIG. 17 shows an example in which an ultrasonic inspection instrument using the sensor 14 suitable for crack detection and crack sizing of the near surface crack 22 is applied to the inconel weld metal 29, the heat affected zone 28 of the shroud support ring and the heat affected zone 26 of the shroud support in the nuclear reactor.

The case (1) in FIG. 16 shows an example in which the ultrasonic inspection instrument using the sensor 14 suitable for crack detection and crack sizing of the near surface crack 22 is applied to the heat affected zone 28 of the shroud support ring. As is understood from FIG. 16, the sensor 14 can be placed on the top of the near surface crack 22 (an opening portion of the crack 22) so as to achieve crack detection and crack sizing applicable to the heat affected portion 28 of the shroud support ring.

The case (3) in FIG. 16 shows an example in which the ultrasonic inspection instrument using the sensor 14 suitable for crack detection and crack sizing of the near surface crack 22 according to the present invention is applied to the heat affected zone 26 of the shroud support. As is understood from FIG. 16, the sensor 14 can be placed on the top of the near surface crack 22 so as to achieve crack detection and crack sizing applicable to the heat affected portion 26 of the shroud support.

Likewise, the case (2) in FIG. 16 shows an example in which the ultrasonic inspection instrument using the sensor 14 suitable for crack detection and crack sizing of the near surface crack 22 is applied to the inconel weld metal 29. As is understood from FIG. 16, the sensor 14 can be placed on the top of the near surface crack 22 so as to achieve crack detection and crack sizing applicable to the inconel weld metal 29.

Particularly in the inconel weld metal 29, the attenuation of ultrasonic waves is large, the ultrasonic waves are redirected, and noise echoes are generated. Thus, crack detection and crack sizing is very difficult in an ultrasonic inspection method using a conventional angle probe or in an ultrasonic inspection method using a conventional TOFD technique, in which the ultrasonic propagation distance in the inconel weld metal 29 is elongated. On the other hand, in the ultrasonic inspection method using the array sensor 14 according to the present invention, crack detection and crack sizing are performed with the array sensor 14 placed on the inconel weld metal 29. Accordingly, there are advantages as follows. (1) The ultrasonic propagation distance in the weld metal can be shortened comparatively so that the efficiency in detecting diffraction echoes is enhanced. (2) Since ultrasonic waves radiated from the array sensor 14 and diffraction echoes coming from the crack tip propagate in substantially the same course even if there is slight influence of redirected ultrasonic waves, and since the array sensor 14 becomes small in size and the transmitter element group and the receiver element group are close to each other, the diffraction echoes can be detected efficiently. Further, in an array sensor in which transmitter elements and receiver elements are disposed alternately as will be described in another embodiment later, the transmitting area and the receiving area of ultrasonic waves can be made substantially identical to each other. Accordingly, the efficiency in detecting diffraction echoes can be prevented from deteriorating due to the influence of redirected ultrasonic waves. Thus, the diffraction echoes can be detected efficiently so that the efficiency in crack detection can be improved exponentially. (3) Due to direct contact, there is no influence of geometric echoes reflected on a portion to be inspected, which geometric echoes cause problems in immersion. Thus, the SN ratio of diffraction echoes is enhanced. That is, the performance of crack detection and crack sizing according to the present invention is improved on a large scale compared with the conventional methods.

A crack sizing method will be described with reference to FIG. 16. By use of a portion having a known thickness t, such as the shroud support 25 in FIG. 16, an ultrasonic wave radiated from the sensor 14 is reflected on the bottom surface as an opposite surface. Thus, the ultrasonic wave returns. Based on the time when the ultrasonic wave is detected, the acoustic velocity in the material can be estimated. Crack sizing can be performed on the basis of the relation between the acoustic velocity and the time when a diffraction echo appears. In addition, as for the inconel weld metal 29 in FIG. 16, in the same manner, by use of a portion having a known thickness t, an ultrasonic wave radiated from the sensor 14 is reflected on the bottom surface as an opposite surface. Thus, the ultrasonic wave returns. Based on the time when the ultrasonic wave is detected, the acoustic velocity in the material can be estimated. Crack sizing can be performed on the basis of the relation between the acoustic velocity and the time when a diffraction echo appears.

The size of the sensor 14 is smaller than or equal to the width of the portion to be inspected or the weld metal as the portion to be inspected. That is, in FIG. 16, Wwel designates the width of the portion to be inspected or the weld metal as the portion to be inspected, and W designates the size (width) of the sensor 14. As is understood from FIG. 16, since the size (width) W of the sensor 14 is smaller than or equal to the width Wwel of the portion to be inspected or the weld metal as the portion to be inspected, for example, ultrasonic waves transmitted from the sensor 14 to thereby inspect the crack 22 in the weld metal as the portion to be inspected do not have to pass through any metallographic structure other than the weld metal. Although FIG. 16 shows the case where there is a step in either end of the weld portion, the same thing can be applied to a double-V groove, a single-V groove or a single bevel groove of welding in a surface having no step. Also in such a case, it is preferable that the size (width) W of the sensor 14 is smaller than or equal to the width Wwel of the portion to be inspected or the weld metal as the portion to be inspected.

FIG. 17 shows an example in which the ultrasonic inspection instrument according to any one of the aforementioned embodiments is applied to inspection near CRD (Control Rod Drive) stub tubes 31 and a pressure vessel 32 in a core bottom portion of a nuclear reactor. An inspection unit 34 capable of storing the sensor 14 and the articulated manipulator 33 of the ultrasonic inspection instrument according to any one of the aforementioned embodiments is retained by a CRD housing 35 and confined by a core plate 36. A signal cable of the sensor 14, a signal cable, a power cable and a high-pressure water hose of the articulated manipulator 33, and so on, are bundled as a cable and hose bundle 37 in the upper portion of the inspection unit 34, and drawn out to an operation floor which is an operation/control site located on the top. Then, the cables and the hoses are connected to their corresponding control units respectively.

A manipulator base portion 38 is fixed to portions above and under the manipulator base portion and to the rotating mechanism 39. Thus, the manipulator base portion 38 has a structure in which the manipulator base portion 38 can perform up-and-down motion and a rotary motion. The manipulator 33 is constituted by three bent joints 40 and two rotary joints 41. A hand 42 is attached to the front end of the manipulator 33. A grip portion 43 attached to the array sensor 14 is gripped by the hand 42. A compliance mechanism 44 is placed between the array sensor 14 and the grip portion 43. The compliance mechanism 44 has a structure allowing the array sensor 14 to follow the curved surfaces of the CRD stub tubes 31, the pressure vessel 32, the weld portions between the CRD stub tubes 31 and the pressure vessel 32, and so on. The compliance mechanism 44 can be displaced in the three X-, Y- and Z-axes. By use of the compliance mechanism 44, the array sensor 14 can be made to smoothly follow the curved surfaces of the CRD stub tubes 31, the pressure vessel 32, the weld portions between the CRD stub tubes 31 and the pressure vessel 32, and so on. As a result, crack detection and crack sizing of the crack 22 can be achieved by use of the aforementioned crack detection and crack sizing method.

Figure 18:
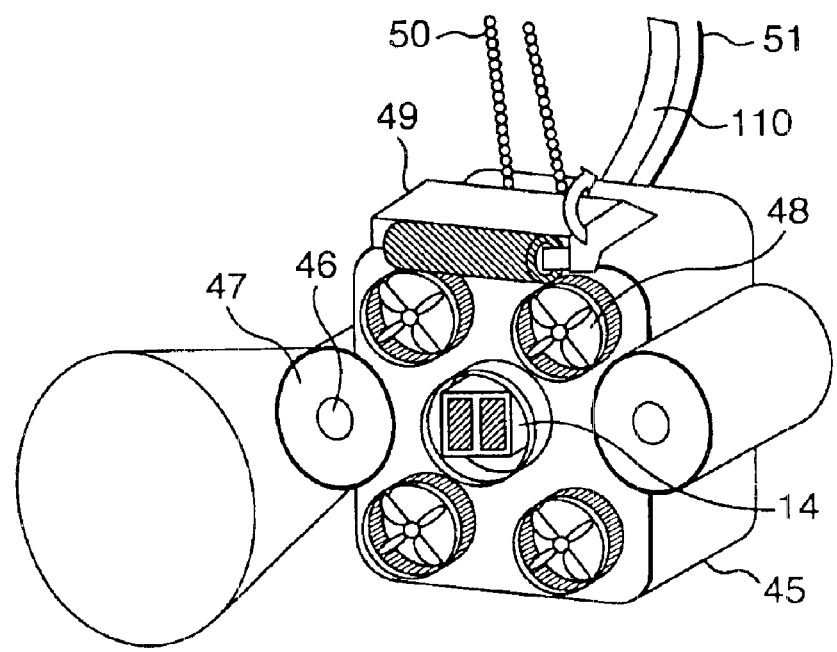
FIG. 18 is a view showing a case in which an array sensor according to the present invention is mounted on a suspended inspection instrument.

FIG. 18 shows an example in which the sensor 14 of the ultrasonic inspection instrument according to any one of the aforementioned embodiments is mounted on a suspended inspection instrument 45, that is, an underwater inspection instrument. The suspended inspection instrument 45 is mounted with the sensor 14, two underwater CCD cameras 46, illuminations 47, thrusters 48 and a crud removing and collecting unit 49.

The suspended inspection instrument 45 is aimed at examining the existence of a crack generated in a general industrial tank, a pool or a core internal structure in a nuclear reactor and performing crack detection and crack sizing through a visual test and an ultrasonic test, which is a nondestructive test. The suspended inspection instrument 45 is suspended by a suspending wire 50. Accordingly, a person in the atmosphere above the suspended inspection instrument 45 can operate the suspending wire 50. By such operation and by use of the thrust force of the thrusters 48, the suspended inspection instrument 45 can be guided to a portion to be inspected so as to bring the sensor 14 into tight contact with the portion to be inspected. Thus, crack detection and crack sizing can be performed by means of the sensor 14.

The two underwater CCD cameras 46 are provided for a visual test. Based on a stereo image reproduced by use of the two underwater CCD cameras 46, an examiner can properly recognize irregularities in the portion to be inspected, and easily determine as to whether the portion to be inspected includes irregularities or a crack (near surface crack). Thus, it is possible to perform a visual test with high visibility and high efficiency. The illuminations 47 serve as light sources for the underwater CCD cameras 46 when the portion to be inspected is dark. A bulb in each illumination 47 is made of a halogen lamp, a metal halide lamp, a light emitting diode or the like, and equipped with a dimmer function for improving the visibility of the underwater CCD camera 46.

The thrusters 48 are thrusters for controlling the posture of the suspended inspection instrument 45. By controlling the rotation direction and the rotation number of each thruster 48, the posture of the suspended inspection instrument 45 can be changed. The crud removing and collecting unit 49 is a unit for removing and sucking deposits such as crud deposited on the portion to be inspected. The crud removing and collecting unit 49 is constituted by a rolling brush for removing deposits and a device for collecting the separated deposits. By removing deposits such as crud or the like by use of the crud removing and collecting unit 49, a crack (near surface crack) lying under the deposits such as crud or the like can be found.

In addition, there is provided a structure in which the removed deposits such as crud or the like are sucked by use of a crud collecting hose 110 and a suction unit, and the sucked deposits such as crud or the like are collected by a filter. As a result, since no turbidity of water occurs, the visual test can be carried out efficiently. Crack detection and crack sizing can be achieved when the suspended inspection instrument 45 is applied to a visual test and an ultrasonic test, which is a nondestructive test, upon a crack generated in a general industrial tank, a pool or a core internal structure in a nuclear reactor. Further, when the suspended inspection instrument 45 is operated remotely while being allowed to swim in a self-propelled manner, the mobility of the suspended inspection instrument 45 is enhanced, and the inspection range is expanded. That is, the underwater inspection instrument mounted with the sensor 14, the two underwater CCD cameras 46, the illuminations 47, the thrusters 48 and the crud removing and collecting unit 49 may be allowed to swim in a self-propelled manner and to be operated remotely. On that occasion, a structure shown in FIG. 20 can be adopted as the fundamental structure of the underwater inspection instrument.

Figure 19:
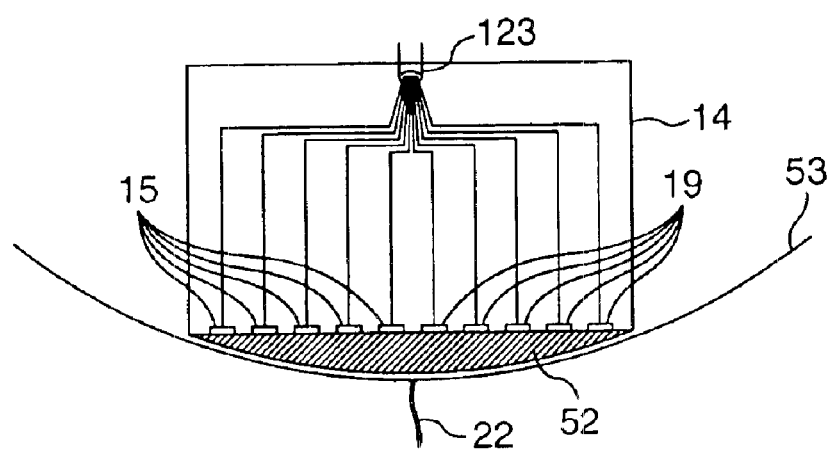
FIG. 19 is a view of Example 1 in which an array sensor according to the present invention is applied to a concave portion to be inspected.

An ultrasonic transmitting/receiving surface (also referred to as "ultrasonic entrance/exit surface") of the sensor 14 facing a subject to be inspected is flat in the ultrasonic inspection instrument according to any one of the aforementioned embodiments. However, as will be explained below, the ultrasonic transmitting/receiving surface does not have to be flat depending on the shape of the surface to be inspected. That is, examples in which the ultrasonic transmitting/receiving surface is formed into a shape other than a flat shape will be described below. FIG. 19 shows an example of the shape of the ultrasonic transmitting/receiving surface of the sensor 14 when a portion 53 to be inspected has a concave shape. When the contact surface of the sensor 14 in contact with the portion 53 to be inspected is flat in the case where the portion 53 to be inspected has a concave shape, a space is formed between the contact surface of the sensor 14 and the surface of the portion 53 to be inspected. As a result, the ultrasonic incident efficiency to the portion 53 to be inspected may deteriorate.

In order to prevent the ultrasonic incident efficiency from deteriorating thus, a wedge 52 made of acryl, polyethylene, etc. and having a surface shape formed into a part of a cylindrical shape or a spherical shape is attached to the ultrasonic entrance/exit surface of the sensor 14. When this wedge 52 is fitted to the shape of the portion 53 to be inspected, the ultrasonic incident efficiency can be prevented from deteriorating. As for the shape of the wedge 52, the radius of the shape of the wedge 52 is made smaller than the radius of the concave shape of the portion 53 to be inspected. In this manner, the performance of the wedge 52 following the portion 53 to be inspected is improved. Thus, the ultrasonic incident efficiency can be prevented from deteriorating, so that ultrasonic inspection with high reliability and high accuracy can be achieved.

Figure 20:
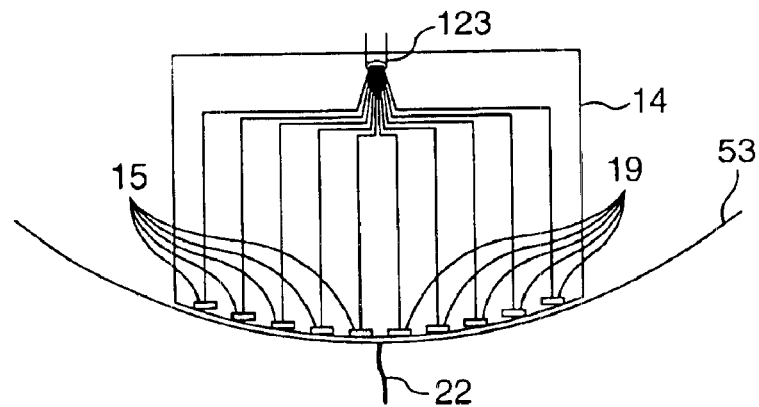
FIG. 20 is a view of Example 2 in which the array sensor according to the present invention is applied to a concave portion to be inspected.

FIG. 20 also shows an example of the sensor 14 for the case where the portion 53 to be inspected has a concave shape. FIG. 20 differs from FIG. 19 in that elements of the transmitter element array 15 and the receiver element array 19 are disposed to follow the shape of the portion 53 to be inspected. Thus, the ultrasonic incident efficiency can be prevented from deteriorating and ultrasonic inspection with high reliability and high accuracy can be achieved, in the same manner as in FIG. 19.

Figure 21:
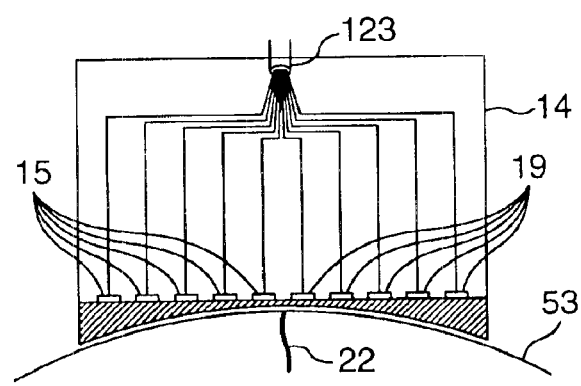
FIG. 21 is a view of Example 1 in which the array sensor according to the present invention is applied to a convex portion to be inspected.

FIG. 21 shows an example of the sensor 14 adapted for the case where the portion 53 to be inspected has a convex shape. When the contact surface of the sensor 14 in contact with the portion 53 to be inspected is flat while the portion 53 to be inspected has a convex shape, a space is formed between the contact surface of the sensor 14 and the portion 53 to be inspected. As a result, the ultrasonic incident efficiency to the portion 53 to be inspected may deteriorate. In order to prevent the ultrasonic incident efficiency from deteriorating thus, a wedge 52 made of acryl, polyethylene etc. and having a surface shape formed into a part of a cylindrical shape or a spherical shape is attached to the ultrasonic entrance/exit surface of the sensor 14. When this wedge 52 is fitted to the shape of the portion 53 to be inspected, the ultrasonic incident efficiency can be prevented from deteriorating. As for the shape of the wedge 52, the radius of the shape of the wedge 52 is made smaller than the radius of the convex shape of the portion 53 to be inspected. As a result, the performance of the wedge 52 following the portion 53 to be inspected is improved. Thus, the ultrasonic incident efficiency can be prevented from deteriorating, so that ultrasonic inspection with high reliability and high accuracy can be achieved.

Figure 22:
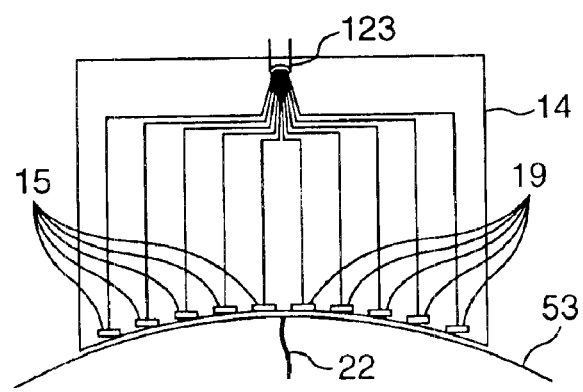
FIG. 22 is a view of Example 2 in which the array sensor according to the present invention is applied to a convex portion to be inspected.

FIG. 22 also shows an example of the sensor 14 for the case where the portion 53 to be inspected has a convex shape. FIG. 22 differs from FIG. 21 in that elements of the transmitter element array 15 and the receiver element array 19 are disposed like a bow so as to be fitted to the shape of the portion 53 to be inspected. Thus, the ultrasonic incident efficiency can be prevented from deteriorating and ultrasonic inspection with high reliability and high accuracy can be achieved, in the same manner as in FIG. 21.

Figure 23:
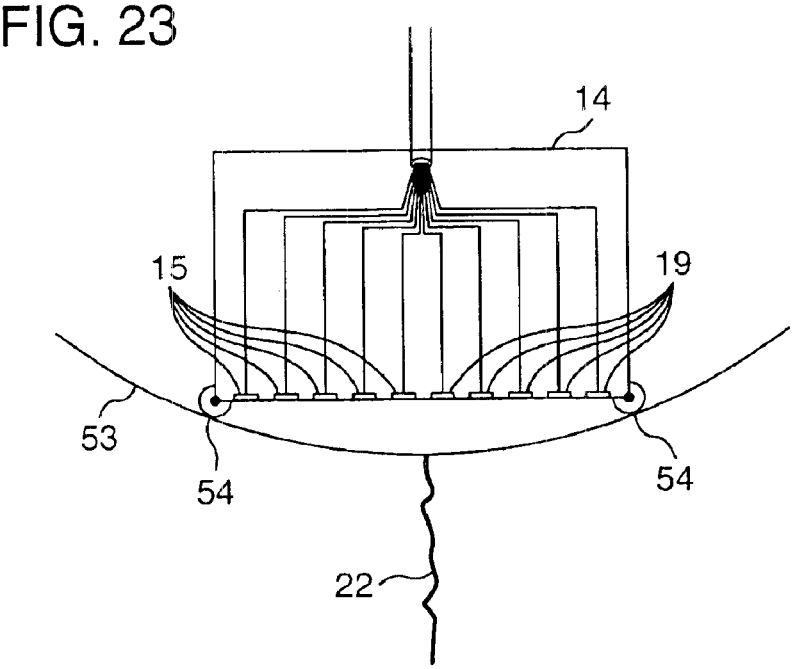
FIG. 23 is a view of an example of a mechanism for allowing the array sensor according to the present invention to follow up a concavo-convex shape.

In FIG. 23, a follow-up performance improving mechanism for improving the performance of the sensor 14 following the portion 53 to be inspected is added to the sensor 14 of the ultrasonic inspection instrument according to any one of the aforementioned embodiments. When inspection is performed with the sensor 14 scanning the portion 53 to be inspected having irregularities, an end portion of the sensor 14 may interfere with the portion 53 to be inspected so that the sensor 14 cannot carry out smooth scanning or come into proper tight contact with the portion 53 to be inspected.

In order to avoid such a phenomenon, sliding mechanisms 54 such as rollers or ball bearings are attached to the end portions of the sensor 14 as friction reduction means, so as to prevent the end portions of the sensor 14 from interfering with or bumping to the portion 53 to be inspected. As a result, smooth scanning of the sensor 14 or proper tight contact of the sensor 14 with the portion 53 to be inspected can be obtained so that ultrasonic inspection with high reliability and high accuracy can be achieved.

Figure 24:
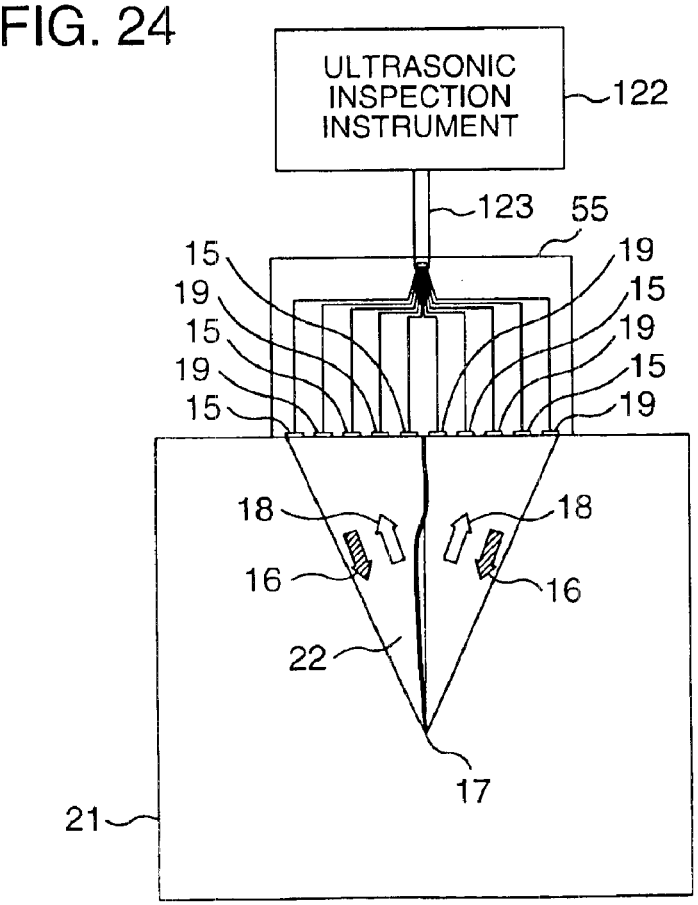
FIG. 24 is a view showing another example in which an ultrasonic inspection instrument according to the present invention is applied to crack detection and crack sizing.

FIG. 24 shows an example of a sensor 55 obtained by devising the arrangement of the elements of the transmitter element array and the receiver element array of the sensor 14 in the ultrasonic inspection instrument according to any one of the aforementioned embodiments. The instrument configuration and the control system in the example of FIG. 24 are the same as those in FIG. 1. The devised point is just as follows. That is, in FIG. 24, the sensor 55 is formed to have the elements of the transmitter element array 15 and the elements of the receiver element array 19 disposed alternately. The sensor 55 is advantageous as follows. That is, since ultrasonic waves radiated from the array sensor 55 and diffraction echoes 18 coming from the crack tip propagate in one and the same course even when there is a slight influence of the ultrasonic waves redirected during propagation through a weld metal or an uneven material, and since the transmitting area of the ultrasonic waves can be made quite identical to the receiving area, the detection efficiency of the diffraction echoes can be prevented from deteriorating due to the influence of the redirected ultrasonic waves. Thus, the diffraction echoes are detected efficiently so that the crack detection efficiency can be improved exponentially.

Figure 25:
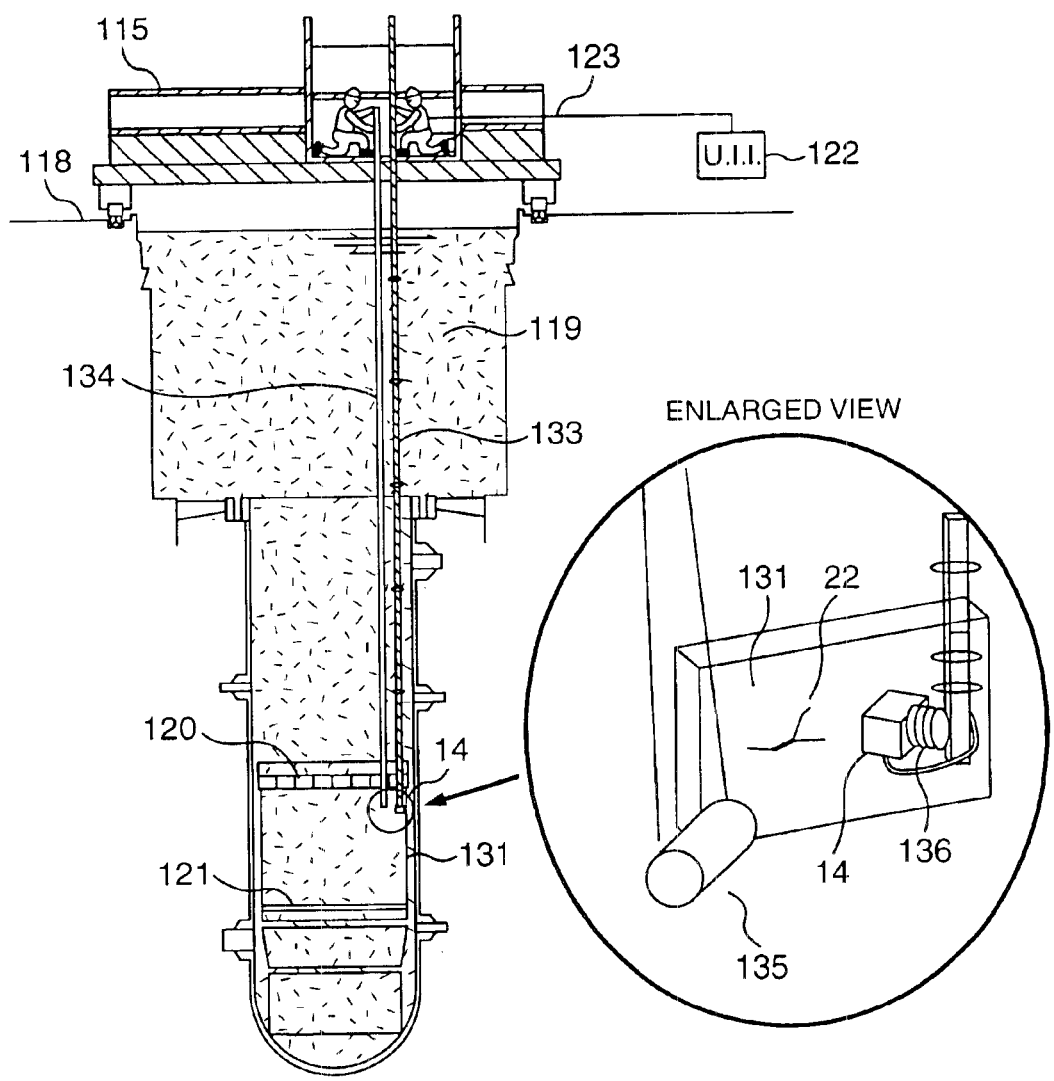
FIG. 25 is a view of an example of a reactor simple inspection instrument using an ultrasonic inspection instrument according to the present invention.

FIG. 25 shows an inspection instrument in a nuclear reactor using the ultrasonic inspection instrument according to any one of the aforementioned embodiments. That is, FIG. 25 shows an embodiment in which the sensor 14 or 55 of the ultrasonic inspection instrument according to any one of the aforementioned embodiments is attached to the lower tip of a rod-like handling pole 133 so as to perform sizing of crack depth in the nuclear reactor. An example in which the sensor 14 is adopted will be described below representatively. The sensor 14 is attached to the lower tip of the handling pole 133. The lower portion of the handling pole 133 is brought down from a service truck 115 on an operation floor 118 into reactor water 119 in a pressure vessel of the nuclear reactor. The sensor 14 is aligned with a crack 22 as follows. That is, the sensor 14 is aligned just above the crack 22 (an opening portion of the crack 22) of a reactor core internal structure 131 such as a shroud etc. in the pressure vessel of the nuclear reactor while being monitored with an illumination-including immersion camera 135 immersed into the reactor water 119 in the pressure vessel of the nuclear reactor substantially simultaneously with the handling pole 133 provided with the sensor 14. A camera cable 134 of the illumination-including immersion camera 135 is connected to a monitor on the service truck 115 so that the position of the sensor 14 can be monitored on the service truck 115 through the monitor.

After the sensor 14 is aligned just above the crack 22 (the opening portion of the crack 22), detection and depth sizing of the crack 22 can be performed by an ultrasonic inspection instrument body 122 connected to the sensor 14 through the signal cable 123. In order to bring the sensor 14 into tight contact with the surface of the crack 22 (reactor core internal structure 131), a fitting mechanism 136 (compliance mechanism or gimbal mechanism) is placed between the handling pole 133 and the sensor 14. Further, when an X-Y scanner is installed between the handling pole 133 and the array sensor 14, the distribution of cracks can be measured.

Figure 26:
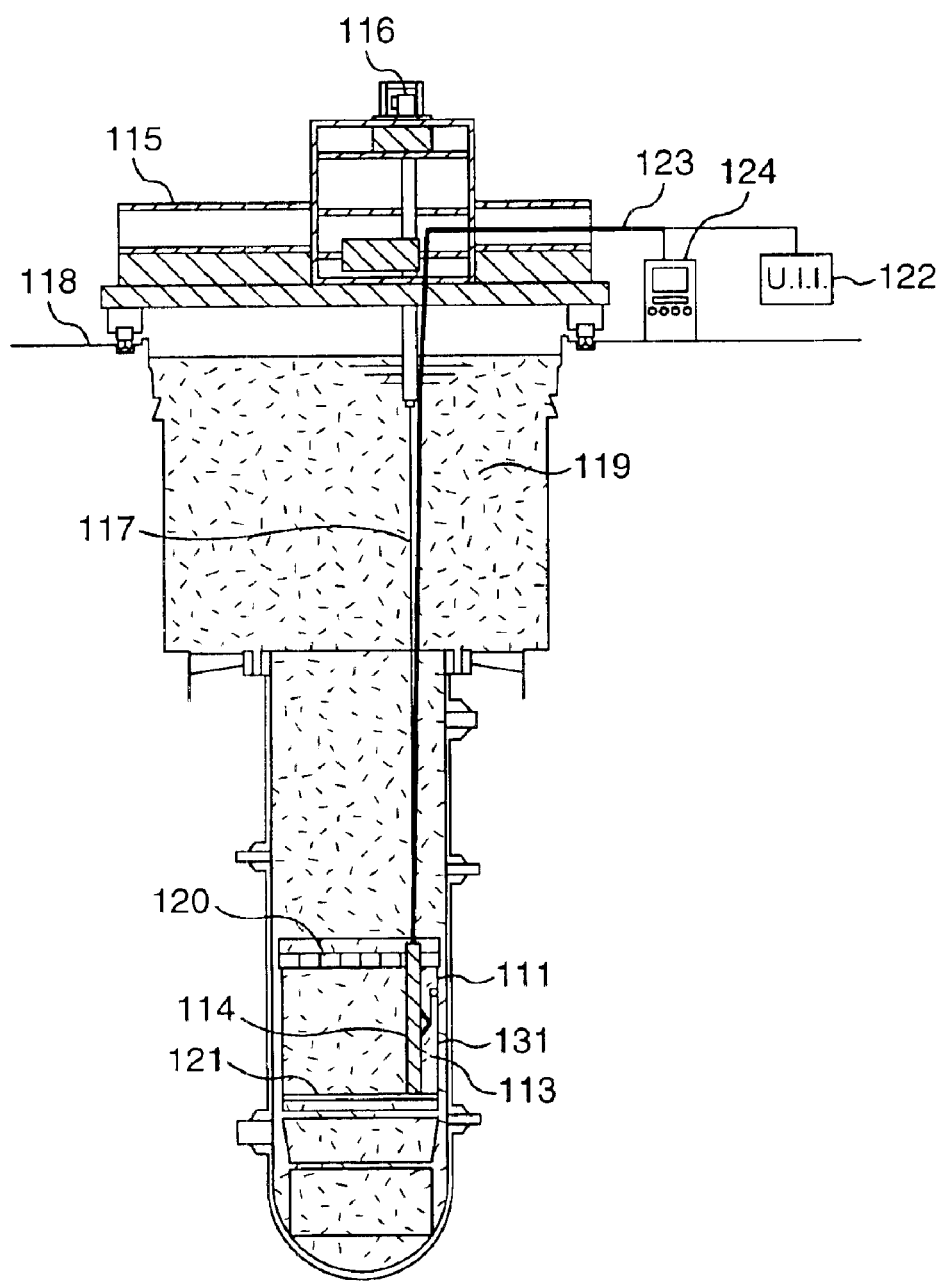
FIG. 26 is a view of an example of a reactor inspection instrument using an ultrasonic inspection instrument according to the present invention.

Another inspection instrument in the nuclear reactor using the ultrasonic inspection instrument according to any one of the aforementioned embodiments will be described below with reference to FIG. 26. An inspection/repair unit 114 (hereinafter referred to as "mast 114") suspended with a wire 117 from an up/down motion mechanism 116 on a service truck 115 on an operation floor 118 is brought down from the service truck 115 into reactor water 119 in a pressure vessel of the nuclear reactor. The mast 114 brought down into the reactor water 119 is seated on a core plate 121 in the pressure vessel of the nuclear reactor, and supported by a top guide 120 in the pressure vessel of the nuclear reactor. A pantograph mechanism 113 serving as an extensible/retractable link mechanism is placed on the mast 114, and an inspection head 111 including the sensor 14 is attached to the front end of the pantograph mechanism 113. Therefore, when the pantograph mechanism 113 is extended, the pantograph mechanism 113 is retracted so that the inspection head 111 including the sensor 14 and stored in the mast 114 projects horizontally. In such a manner, the sensor 14 can move forward/backward from the mast 114 by the extension/retraction operation of the pantograph mechanism 113.

The sensor 14 is pressed onto the reactor core internal structure 131 in the nuclear reactor by the extension operation of the pantograph mechanism 113 so as to perform crack detection or crack depth sizing. The sensor 14 stored inside the inspection head 111 is pressed onto the reactor core internal structure 131 such as the shroud etc. to be inspected, so as to perform detection and sizing of a crack in the shroud etc. The sensor 14 is retained by a gimbal mechanism placed inside the inspection head 111. The gimbal mechanism is retained by a pressing mechanism, and the pressing mechanism is gripped by an X-Y scanner. That is, the X-Y scanner, the pressing mechanism, the gimbal mechanism and the array sensor 14 are included in the inspection head 111. The pantograph mechanism 113 is supported by a linear motion mechanism inside the mast 114, so that the pantograph 113 can move up/down inside the mast 114 by means of the linear motion mechanism.

Consequently, when detailed inspection is performed upon the shroud etc. as a surface to be inspected or when a measuring point is to be moved slightly, the sensor 14 is moved by use of the X-Y scanner. In addition, when rough inspection is performed or the inspection location is changed largely, the inspection head 111 and the sensor 14 can be moved by the linear motion mechanism and the pantograph mechanism 113 in the mast 114.

Next, description will be made on a method for putting the mast 114 into the pressure vessel of the nuclear reactor and withdrawing the mast 114 therefrom. By use of the wire 117 and the up/down motion mechanism 116 installed on the service truck 115, the mast 114 is suspended from the height of the operation floor 118 and moved down into the reactor water 119. The mast 114 is passed through the top guide 120, and seated on the core plate 121. After that, in the procedure as described above, the inspection head 111 is developed toward the inspection position by the extension/retraction of the pantograph mechanism 113, so that the sensor 14 is pressed onto the shroud etc. as a surface to be inspected, to thereby perform detection and sizing of a crack in the shroud etc. After the termination of the inspection, the inspection head 111 is stored into the mast 114 in a reverse procedure to that for the development of the inspection head 111. The mast 114 is pulled up to the height of the operation floor 118 by the up/down motion mechanism 116 installed on the service truck 115, and taken up onto the operation floor 118 by use of a ceiling crane or the like.

The operations including the rotation of the mast 114, the up/down motion, development and storage of the pantograph mechanism 113, and so on, are controlled by an inspection/repair unit controller 124 on the operation floor 118, and control signals are transmitted through the signal cable 123. The sensor 14 included in the inspection head 111 is controlled by the ultrasonic inspection instrument body 122, and a control signal is transmitted through the cable 123 between the sensor 14 and the ultrasonic inspection instrument body 122.

According to the present invention, ultrasonic inspection can be performed surely even under conditions where the ultrasonic diffraction intensity becomes weak.

It should be further understood by those skilled in the art that although the foregoing description has been made on embodiments of the invention, the invention is not limited thereto and various changes and modifications may be made without departing from the spirit of the invention and the scope of the appended claims.

What is claimed is:

1. An ultrasonic array sensor comprising:
   a transmitter element array in which a plurality of transmitter elements for transmitting ultrasonic waves are arrayed; and
   a receiver element array in which a plurality of receiver elements for receiving ultrasonic waves are arrayed;
   wherein said elements of said element arrays are arrayed so that each of said elements is 0.1 mm to 2 mm wide and adjacent ones of said elements in each of said element arrays are at a distance of 0.05 mm to 0.2 mm from each other.

2. An ultrasonic array sensor according to claim 1, wherein said elements of said element arrays are arrayed in a range surrounded by 30 mm width of said array sensor in an array direction of said elements and 30 mm depth of said array sensor in a length direction of said elements perpendicular to said array direction.

3. An ultrasonic array sensor according to claim 1, wherein said transmitter elements and said receiver elements are disposed alternately.

4. An ultrasonic array sensor according to claim 1, wherein an entrance/exit surface of ultrasonic waves has a surface shape formed into a part of a cylindrical shape or a spherical shape.

5. An ultrasonic inspection instrument comprising:
   an array sensor having both a transmitter element array in which a plurality of transmitter elements for transmitting ultrasonic waves are arrayed and a receiver element array in which a plurality of receiver elements for receiving ultrasonic waves are arrayed;
   a control unit for focusing ultrasonic waves transmitted from said transmitter elements respectively on a focus point where half the sum of a transmitting angle and a receiving angle will be not larger than 30 degrees;
   a generation unit for generating inspection information based on said ultrasonic waves received by said receiver elements; and
   a display unit for displaying said inspection information generated by said generation unit.

6. An ultrasonic inspection instrument according to claim 5, further comprising a control unit for moving said focus point electronically to a range including said position where half the sum of a transmitting angle and a receiving angle will be not larger than 30 degrees.

7. An ultrasonic inspection instrument according to claim 5, wherein the elements of said element arrays are arrayed so that each of said elements is 0.1 mm to 2 mm wide and adjacent ones of said elements in each of said element arrays are at a distance of 0.05 mm to 0.2 mm from each other.

8. An ultrasonic inspection instrument according to claim 5, further comprising a first amplification control unit for changing amplification of a signal to be supplied to each of said transmitter elements in accordance with said focus point.

9. An ultrasonic inspection instrument according to claim 5, further comprising a second amplification control unit for changing amplification of a signal to be supplied from each of said receiver elements in accordance with said focus point.

10. An ultrasonic inspection instrument according to claim 5, wherein said array sensor is attached to a handling pole.

11. An ultrasonic inspection instrument according to claim 5, further comprising:
    a mast supported by a core plate and a top guide in a nuclear reactor; and
    an extensible/retractable link mechanism attached to said mast;
    wherein said array sensor is attached to said link mechanism.

12. An ultrasonic inspection instrument according to claim 5, further comprising:
    a mast supported by a core plate and a top guide in a nuclear reactor; and
    an articulated manipulator attached to said mast;
    wherein said array sensor is attached to said articulated manipulator.

13. An ultrasonic inspection instrument according to claim 5, further comprising:
    an inspection unit having an illuminator for illuminating a subject to be inspected, imaging device for imaging said subject to be inspected, a unit for removing crud from said subject to be inspected, said removing unit for sucking and collecting said crud, and an underwater thruster;

wherein said array sensor is attached to said inspection unit.

14. An ultrasonic inspection method for controlling an ultrasonic inspection instrument comprising the steps of:

transmitting and receiving ultrasonic waves to and from a subject to be inspected, by means of an array sensor having both a transmitter element array in which a plurality of transmitter elements for transmitting ultrasonic waves are arrayed and a receiver element array in which a plurality of receiver elements for receiving ultrasonic waves are arrayed; and focusing said ultrasonic waves on a focus point where half the sum of a transmitting angle and a receiving angle involved in said transmission and reception is not larger than 30 degrees.

15. An ultrasonic inspection method according to claim 14, the elements of said element arrays are arrayed so that each of said elements is 0.1 mm to 2 mm wide and adjacent ones of said elements in each of said element arrays are at a distance of 0.05 mm to 0.2 mm from each other.

16. An ultrasonic inspection method according to claim 14, wherein a central portion of said array sensor is aligned with a position opposed to an opening portion of a near surface crack of said subject to be inspected, and said ultrasonic waves are thereafter transmitted to and received from said subject to be inspected whenever a focus point of said ultrasonic waves is moved for electronically scanning said subject to be inspected.

17. An ultrasonic inspection method according to claim 16, wherein amplification of a signal to be supplied to each of said transmitter elements or a signal to be supplied from each of said receiver elements is increased with increase of a distance between said focus point and said array sensor.

18. An ultrasonic inspection method according to claim 14, wherein said array sensor is attached to a handling pole, an articulated manipulator, a link mechanism or an underwater inspection unit, and said handling pole, said articulated manipulator, said link mechanism or said underwater inspection unit is operated to move said array sensor to an inspection position of said subject to be inspected.

19. An ultrasonic inspection method according to claim 14, wherein an array sensor having a foot print on said subject to be inspected is used as said array sensor, said foot print being equal to or smaller than width of said subject to be inspected.

20. An ultrasonic inspection instrument comprising:

an array sensor having both a transmitter element array in which a plurality of transmitter elements for transmitting ultrasonic waves are arrayed and a receiver element array in which a plurality of receiver elements for receiving ultrasonic waves are arrayed;

a control unit for focusing ultrasonic waves transmitted from said transmitter elements on a focus point;

an amplification control unit for changing amplification of at least one of a signal to be supplied to each of said transmitter elements and a signal to be supplied from each of said receiver elements, in accordance with said focus point;

a generation unit for generating inspection information based on said ultrasonic waves received by said receiver elements; and a display unit for displaying said inspection information generated by said generation unit.

* * * * *